US009168329B2

(12) United States Patent
Palecek et al.

(10) Patent No.: US 9,168,329 B2
(45) Date of Patent: *Oct. 27, 2015

(54) BETA-PEPTIDES WITH ANTIFUNGAL ACTIVITY

(75) Inventors: Sean P. Palecek, Verona, WI (US); Samuel H. Gellman, Madison, WI (US); William C. Pomerantz, Madison, WI (US); Amy J. Karlsson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1322 days.

This patent is subject to a terminal disclaimer.

(21) Appl. No.: 11/849,751

(22) Filed: Sep. 4, 2007

(65) Prior Publication Data

US 2008/0166388 A1 Jul. 10, 2008

Related U.S. Application Data

(60) Provisional application No. 60/841,718, filed on Sep. 1, 2006.

(51) Int. Cl.
| | |
|---|---|
| *C07K 5/023* | (2006.01) |
| *A61L 31/16* | (2006.01) |
| *A61L 27/54* | (2006.01) |
| *A61L 29/16* | (2006.01) |
| *C07K 5/02* | (2006.01) |
| *A61K 38/00* | (2006.01) |

(52) U.S. Cl.
CPC .................. *A61L 31/16* (2013.01); *A61L 27/54* (2013.01); *A61L 29/16* (2013.01); *A61K 38/00* (2013.01); *A61L 2300/252* (2013.01); *C07K 5/0202* (2013.01)

(58) Field of Classification Search
None
See application file for complete search history.

(56) References Cited

U.S. PATENT DOCUMENTS

| 6,613,876 | B1 * | 9/2003 | Gellman et al. | 506/18 |
| 6,677,431 | B2 * | 1/2004 | DeGrado et al. | 530/326 |
| 2003/0032599 | A1 * | 2/2003 | Lipkowski et al. | 514/15 |
| 2005/0282755 | A1 * | 12/2005 | Hart et al. | 514/14 |

FOREIGN PATENT DOCUMENTS

| WO | WO 01/32020 | * | 5/2001 |
| WO | WO 2007/147002 | * | 12/2007 |

OTHER PUBLICATIONS

Gal (Journal of Chromatography A 'On the meaning and use of homochiral' (1998) 829, 417-418).*
Raguse et al (J Am Chem Soc 'Structure-activity studies of 14-helical antimicrobial beta-peptides: probing the relationship between conformational stability and antimicrobial potency' (2002) 124:12774-12785).*
Karlsson et al (J Am Chem Soc 'Antifungal activity from 14-helical-beta-peptides' (2006) 128:12630-12631).*
Shalev et al (Journal of Biological Chemistry 'Consequences of N-acylation on structure and membrane binding properties of dermaseptin derivative K4-S4-(1-13)' (2006) 281:9432-9438).*
Hamuro et al ('De novo design of antibacterial beta-peptides' J Am. Chem. Soc. v121 1999 pp. 12200-12201).*
Bruckner et al ('Molecular architecture with functionalized beta-peptide helices' Angew. Chem. Int. Ed. V42 2003 pp. 4395-4399).*
Shih et al ('Hydrophobicities of the nucleic acid bases:distribution coefficients from water to cyclohexane' J Mol Biol v280 1998 pp. 421-430).*
Kasabe et al ('Synthesis,characterization and primary antimicrobial, antifungal activity evaluation of Schiff bases of 4-chloro-(3-substiut-ted-phenylimino)-methyl[2H]-chromine-2-one' E-journal of chemistry v7(2) 2010 pp. 377-382).*
Groot et al ('Histatin 5-derived peptide with improved fungicidal properties enhances human immunodeficiency virus type 1 replication by promoting viral entry' Journal of virology v80(18) Sep. 2006 pp. 9236-9243).*
Radzishevsky et al ('Effects of acyl versus aminoacyl conjugation on the properties of antimicrobial peptides' Antimicrobial agents and chemotherapy v49(6) 2005 pp. 2412-2420).*
Schmitt et al ('Unexpected relationships between structure and function in alpha-beta-peptides:antimicrobial foldamers with heterogeneous backbones' JACS v126 2004 pp. 6848-6849).*
Creighton, Proteins; Structures and Molecular Principles 2nd ed., 1993, 14.

* cited by examiner

*Primary Examiner* — James H Alstrum Acevedo
*Assistant Examiner* — Ronald Niebauer
(74) *Attorney, Agent, or Firm* — Joseph T. Leone, Esq.; DeWitt Ross & Stevens S.C.

(57) ABSTRACT

The present invention is directed to the design, synthesis and use of various β-peptides exhibiting antifungal activity. The β-peptides are relatively short in length, adopt globally amphiphilic conformations, and cause little lysis of human red blood cells at concentrations that kill *Candida albicans*, a common human fungal pathogen.

6 Claims, 26 Drawing Sheets

Cecropin B and magainin peptides are not active against *C. albicans*

| Drug | Strain | MIC (µg/ml) | MIC (µM) |
|---|---|---|---|
| Amphotericin B | SC5314 | 1 | 1.1 |
| | ATCC 24433 | 1 | 1.1 |
| | ATCC 90028 | 1 | 1.1 |
| Magainin 2 | SC5314 | >128 | >52 |
| | ATCC 24433 | >128 | >52 |
| | ATCC 90028 | >128 | >52 |
| (Ala⁸¹⁵,¹⁸) Magainin 2 amide | SC5314 | >128 | >52 |
| | ATCC 24433 | >128 | >52 |
| | ATCC 90028 | >128 | >52 |
| Cecropin B | SC5314 | >128 | >33 |
| | ATCC 24433 | >128 | >33 |
| | ATCC 90028 | >128 | >33 |

Fig. 1

Planktonic testing: Effect of length on ACHC-V-K series

| Drug | Strain | MIC (µg/ml) | MIC (µM) |
| --- | --- | --- | --- |
| (ACHC-$\beta^3$Val-$\beta^3$Lys)$_2$ | SC5314 | >128 | >114 |
| | ATCC 24433 | >128 | >114 |
| | ATCC 90028 | >128 | >114 |
| $\beta^3$Tyr-(ACHC-$\beta^3$Val-$\beta^3$Lys)$_2$ | SC5314 | >128 | >98.7 |
| | ATCC 24433 | >128 | >98.7 |
| | ATCC 90028 | >128 | >98.7 |
| (ACHC-$\beta^3$Val-$\beta^3$Lys)$_3$ | SC5314 | 16 | 9.9 |
| | ATCC 24433 | 32 | 19.8 |
| | ATCC 90028 | 16 | 9.9 |
| $\beta^3$Tyr-(ACHC-$\beta^3$Val-$\beta^3$Lys)$_3$ | SC5314 | 16 | 8.9 |
| | ATCC 24433 | 16 | 8.9 |
| | ATCC 90028 | 16 | 8.9 |
| $\beta^3$Tyr-(ACHC-$\beta^3$Val-$\beta^3$Lys)$_4$ | SC5314 | >128 | >56 |
| | ATCC 24433 | >128 | >56 |
| | ATCC 90028 | >128 | >56 |

Fig. 5

Planktonic testing: N-terminal tyrosine can affect activity
(ACHC-β³Val-β³Lys)₃
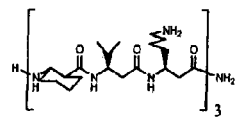
(ACHC-ACHC-β³Lys)₃
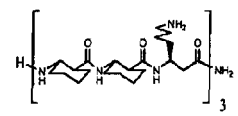
β³Tyr-(ACHC-β³Val-β³Lys)₃
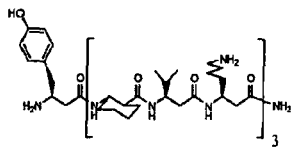
β³Tyr-(ACHC-ACHC-β³Lys)₃
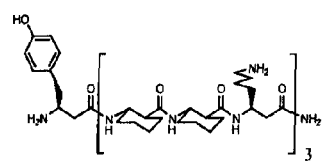
| Drug | Strain | MIC | |
|---|---|---|---|
| | | µg/ml | µM |
| (ACHC-β³Val-β³Lys)₃ | SC5314 | 16 | 9.9 |
| | ATCC 24433 | 32 | 19.8 |
| | ATCC 90028 | 16 | 9.9 |
| β³Tyr-(ACHC-β³Val-β³Lys)₃ | SC5314 | 16 | 8.9 |
| | ATCC 24433 | 16 | 8.9 |
| | ATCC 90028 | 16 | 8.9 |
| Drug | Strain | MIC | |
|---|---|---|---|
| | | µg/ml | µM |
| (ACHC-ACHC-β³Lys)₃ | SC5314 | 64 | 39 |
| | ATCC 24433 | 64 | 39 |
| | ATCC 90028 | 64 | 39 |
| β³Tyr-(ACHC-ACHC-β³Lys)₃ | SC5314 | 16 | 8.8 |
| | ATCC 24433 | 32 | 17.5 |
| | ATCC 90028 | 16 | 8.8 |
Fig. 6

Planktonic testing: "Scrambled" peptides are not active

Amphiphilic

Scrambled

| Drug | Strain | MIC | |
|---|---|---|---|
| | | µg/ml | µM |
| (ACHC-β³Val-β³Lys)₃ | SC5314 | 16 | 9.9 |
| | ATCC 24433 | 32 | 19.8 |
| | ATCC 90028 | 16 | 9.9 |
| β³Lys-(β³Val)₂-ACHC-β³Lys-β³Val-ACHC₂-β³Lys | SC5314 | >128 | >79 |
| | ATCC 24433 | >128 | >79 |
| | ATCC 90028 | >128 | >79 |

| Drug | Strain | MIC | |
|---|---|---|---|
| | | µg/ml | µM |
| β³Tyr-(ACHC-ACHC-β³Lys)₃ | SC5314 | 16 | 8.8 |
| | ATCC 24433 | 32 | 17.5 |
| | ATCC 90028 | 16 | 8.8 |
| β³Tyr-ACHC-(ACHC-β³Lys)₃-ACHC-ACHC | SC5314 | >128 | >70 |
| | ATCC 24433 | >128 | >70 |
| | ATCC 90028 | >128 | >70 |

Fig. 9

Planktonic testing: Varying middle residue side chain varies MIC
| Drug | | Strain | MIC (µg/ml) | MIC (µM) |
|---|---|---|---|---|
| β³Tyr-(ACHC-β³Val-β³Lys)₃ | 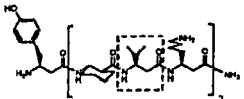 | SC5314 | 16 | 8.9 |
| | | ATCC 24433 | 16 | 8.9 |
| | | ATCC 90028 | 16 | 8.9 |
| β³Tyr-(ACHC-ACHC-β³Lys)₃ |  | SC5314 | 16 | 8.8 |
| | | ATCC 24433 | 32 | 17.5 |
| | | ATCC 90028 | 16 | 8.8 |
| β³Tyr-(ACHC-β³Leu-β³Lys)₃ | 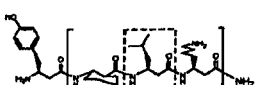 | SC5314 | 8 | 4.4 |
| | | ATCC 24433 | 16 | 8.7 |
| | | ATCC 90028 | 16 | 8.7 |
| β³Tyr-(ACHC-β³Phe-β³Lys)₃ | 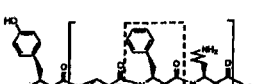 | SC5314 | 8 | 4.1 |
| | | ATCC 24433 | 8 | 4.1 |
| | | ATCC 90028 | 8 | 4.1 |
| β³Tyr-(ACHC-β³Lys-β³Lys)₃ |  | SC5314 | >128 | >57.6 |
| | | ATCC 24433 | >128 | >57.6 |
| | | ATCC 90028 | >128 | >57.6 |
Fig. 10

Planktonic testing: Activity is maintained when positively-charged residue is changed

| Drug | Strain | MIC (µg/ml) | MIC (µM) |
|---|---|---|---|
| β³Tyr-(ACHC-β³Val-β³Lys)₃ | SC5314 | 16 | 8.9 |
|  | ATCC 24433 | 16 | 8.9 |
|  | ATCC 90028 | 16 | 8.9 |
| β³Tyr-(ACHC-β³Val-β³Arg)₃ | SC5314 | 16 | 8.5 |
|  | ATCC 24433 | 16 | 8.5 |
|  | ATCC 90028 | 16 | 8.5 |

Fig. 11

Planktonic testing: Incorporating ACHC enantiomer eliminates activity

| Drug | Strain | MIC (µg/ml) | MIC (µM) |
|---|---|---|---|
| β³Tyr-[(R,R)ACHC-β³Val-β³Lys]₃ | SC5314 | >128 | >71 |
| | ATCC 24433 | >128 | >71 |
| | ATCC 90028 | >128 | >71 |
| β³Tyr-[(S,S)ACHC-β³Val-β³Lys]₃ | SC5314 | 16 | 8.9 |
| | ATCC 24433 | 16 | 8.9 |
| | ATCC 90028 | 16 | 8.9 |

Fig. 12

Growth reduction from Y-(ACHC-ACHC-K)$_3$

Fig. 17

Planktonic testing: Amphiphilic sequence isomers have similar activity

| Drug | Strain | MIC (μg/ml) | MIC (μM) |
|---|---|---|---|
| β3Tyr-(ACHC-β3Leu-β3Lys)3 | SC5314 | 8 | 4.4 |
| β3Tyr-(β3Leu-ACHC-β3Lys)3 | SC5314 | 16 | 8.7 |

Fig. 18

Planktonic testing: $\beta^3$Tyr-(ACHC-$\beta^3$Phe-$\beta^3$Lys)$_3$ enantiomers have similar activity

| Drug | Strain | MIC (μg/ml) |
| --- | --- | --- |
| (R)$\beta^3$Tyr-[(R,R)ACHC-(R)$\beta^3$Phe-(R)$\beta^3$Lys]$_3$ | SC5314 | 8 |
| | ATCC 24433 | 8 |
| | ATCC 90028 | 8 |
| (S)$\beta^3$Tyr-[(S,S)ACHC-(S)$\beta^3$Phe-(S)$\beta^3$Lys]$_3$ | SC5314 | 8 |
| | ATCC 24433 | 8 |
| | ATCC 90028 | 8 |

Fig. 19

Planktonic testing: β-peptide charge affects activity

- β³Lys is +1, β³Lys is -1, N-terminus is +1
- +7 and +2 β-peptides do not kill C. albicans
- Anionic β-peptide does not kill C. albicans

| Drug | Charge | Strain | MIC (µg/ml) | MIC (µM) |
|---|---|---|---|---|
| β³Tyr-(ACHC-ACHC-β³Lys)₃ | +4 | SC5314 | 16 | 8.8 |
| β³Tyr-ACHC-ACHC-ACHC-β³Glu-(ACHC-ACHC-β³Lys)₂ | +2 | SC5314 | >128 | >86 |
| β³Tyr-ACHC-ACHC-ACHC-β³Lys-ACHC-ACHC-β³Glu-ACHC-ACHC-β³Lys | +2 | SC5314 | >128 | >86 |
| β³Tyr-(ACHC-ACHC-β³Glu)₃ | -2 | SC5314 | >128 | >74.6 |

Fig. 20

Planktonic testing: Acylation of β³Tyr-(ACHC-ACHC-β³Lys)₃

| Drug | Strain | MIC (µg/ml) |
|---|---|---|
| β³Tyr-(ACHC-ACHC-β³Lys)₃ | SC5314 | 16 |
| | ATCC 24433 | 32 |
| | ATCC 90028 | 16 |
| C9-β³Tyr-(ACHC-ACHC-β³Lys)₃ (nonanoic acid added) | SC5314 | 16 |
| | ATCC 24433 | 16 |
| | ATCC 90028 | 16 |
| C15-β³Tyr-(ACHC-ACHC-β³Lys)₃ (pentadecanoic acid added) | SC5314 | >128 |
| | ATCC 24433 | >128 |
| | ATCC 90028 | >128 |

Summary of planktonic MIC and hemolysis results

| Peptide | Average MIC (μg/mL) | % Hemolysis at average MIC |
|---|---|---|
| (ACHC-β³Val-β³Lys)₃ | 16.8 | 5 |
| β³Tyr-(ACHC-β³Val-β³Lys)₃ | 16 | 21 |
| β³Tyr-(ACHC-β³Val-β³Lys)₂ | >128 | 5 * |
| β³Tyr-(ACHC-β³Val-β³Lys)₄ | >128 | 21 * |
| β³Tyr-ACHC-(ACHC-β³Lys)₃-ACHC-ACHC | >128 | 2 * |
| (ACHC-ACHC-β³Lys)₃ | 47 | 3 |
| β³Tyr-(ACHC-ACHC-β³Lys)₃ | 21.0 | 7 |
| β³Tyr-(ACHC-β³Leu-β³Lys)₃ | 11 | 73 |
| β³Tyr-(ACHC-β³Phe-β³Lys)₃ | 8 | 80 |
| β³Tyr-(ACHC-β³Lys-β³Lys)₃ | >128 | 5 * |
| β³Tyr-(β³Val-β³Val-β³Lys)₃ | 69.0 | 9 |
| β³Tyr-(ACHC-β³Val-β³Arg)₃ | 16 | 34 |
| L (Ala⁸,¹³,¹⁸) Magainin 2 amide | >128 | 48 * |

\* For peptides with MIC higher than the highest concentration tested (128 μg/mL), the % hemolysis at 128 μg/mL is given

Fig. 22

Results for *C. albicans* strains ATCC 24433 and SC5314 are similar to ATCC 90028.

Biofilm testing: Biofilm formation can be prevented in the presence of and Y-(ACHC-V-K)₃

BETA-PEPTIDES WITH ANTIFUNGAL ACTIVITY

CROSS REFERENCE TO RELATED APPLICATION

This non-provisional application claims the benefit of U.S. Provisional application 60/841,718, filed Sep. 1, 2006, which is incorporated herein by reference in its entirety for all purposes.

STATEMENT REGARDING FEDERALLY SPONSORED RESEARCH AND DEVELOPMENT

This work was supported in part by awards from the United States government-grant DMR-0425880 from the National Science Foundation. The Government of the United States may have certain rights in this invention.

FIELD OF THE INVENTION

This invention is generally directed to compositions and methods for the treatment of fungal infections. In particular, this invention is directed to the design, manufacture and use of β-peptides possessing antifungal activity.

BACKGROUND OF THE INVENTION

Treating fungal infections represents a profound medical challenge. For example, infections by the ubiquitous fungus *Candida albicans*, commonly referred to as yeast infections, can be either systemic or topical and are a persistent health problem in some patient populations. Topical infections, called candidiasis, can infect the mouth ("thrush"), vagina, skin, stomach, and urinary tract. Approximately seventy-five percent of women will get candidiasis of the vagina during their lifetime, and ninety percent of all people with HIV/AIDS develop *Candida* spp. infections. These infections, while typically not life threatening, produce numerous unpleasant side effects and are generally treated with topical antifungal ointments containing clotrimazole or with oral or intravenous medications containing fluconazole or amphotericin B, especially for systemic infections.

Systemic infections, referred to as candidemia and characterized by presence of the organism in the bloodstream, however, are a significant and often life-threatening clinical problem. These infections most commonly occur in the presence of an indwelling medical device (e.g., intravascular catheter) or in immunosuppressed patients. The vast majority of these infections are nosocomial (i.e. occur in the hospital in conjunction with treatment for a primary ailment). Candidemias are associated with significant attributable mortality and prolonged hospitalization. The present choice of antifungal is between azole drugs (most commonly fluconazole) and amphotericin B; the latter typically viewed as more effective but also extremely toxic.

Natural and synthetic small molecule antifungal agents are known, but their use as therapeutics is limited by their inherent toxicity to humans and increasing incidence of resistance. For example, amphotericin B was initially discovered in the 1950s. It causes cell death by inhibiting synthesis of ergosterol, a component of the fungal cell membrane. Amphotericin B must be administered intravenously and can only be given for a limited number of days without leading to kidney or vascular damage or both. Liposomal formulations and micellar formulations have been developed which result in lower toxicity; however these formulations are considerably more expensive than conventional amphotericin B formulations.

Host-defense peptides, components of the innate immune system that are very effective against prokaryotic pathogens, have been reported to display antifungal activity under some conditions in vitro, but the relevance of these results to in vivo activity is unclear. Hydrophobic appendages have been shown to enhance the antifungal activity of host-defense peptides and designed sequences.

Several researchers have explored unnatural oligomers composed of β-amino acids ("β-peptides") as mimics of host-defense α-peptides in the antibacterial context. β-Peptide "foldamers" can be designed to adopt helical conformations that display discrete hydrophobic and cationic surfaces, thereby mimicking the globally amphiphilic α helical conformations of many host-defense peptides, including magainins and cecropins. Some β-peptides have been shown to display antibacterial activity comparable to that of the host-defense α-peptide prototypes. However, the use of β-peptides in the realm of combating fungal pathogens has received little, if any, attention.

As can be appreciated by the foregoing, a need exists for alternative antifungal agents, particularly agents that exhibit low toxicity to the subject.

SUMMARY OF THE INVENTION

The present invention provides relatively short β-peptides (preferably 9 or 10 residues) designed to adopt globally amphiphilic conformations that display significant antifungal activity. The most preferred β-peptides according to the invention cause little lysis of human red blood cells at concentrations that kill *Candida albicans*, a common human fungal pathogen. Since fungi are eukaryotes, discrimination between fungal and human cells is a significant advantage offered by the present invention. As well, β-peptides according to the invention are active under assay conditions that mimic physiological pH and ionic strength; in contrast, α-helix-forming host-defense α-peptides are inactive against *C. albicans* under these conditions.

Accordingly, the invention provides compositions and methods for inhibiting fungal growth. Methods according to the invention include the step of contacting a fungus to be inhibited with an inhibitory amount of a β-peptide. Such β-peptides preferably have the structure:

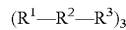

wherein $R^1$, $R^2$, and $R^3$ of each triad are independently selected from β-amino acid residues bearing hydrophobic and cationic side chains such that the $R^1$—$R^2$—$R^3$ triads in the β-peptide consist of β-amino acid residues bearing hydrophobic and cationic side chains in the sequential pattern hydrophobic-hydrophobic-cationic, hydrophobic-cationic-hydrophobic, or cationic-hydrophobic-hydrophobic. It is preferred that β-amino acid residues are homo-chiral and, in certain preferred embodiments, $R^1$ is trans-2-aminocyclohexanecarboxylic acid (ACHC), $R^2$ is ACHC, $β^3$Val, $β^3$Leu, or $β^3$Phe; and $R^3$ is $β^3$Lys or $β^3$Arg. Exemplary β-peptides for use in the invention include, but are not limited to, (ACHC-$β^3$Val-$β^3$Lys)$_3$, $β^3$Tyr-(ACHC-$β^3$Val-$β^3$Lys)$_3$, $β^3$Tyr-(ACHC-$β^3$Leu-$β^3$Lys)$_3$, $β^3$Tyr-(ACHC-$β^3$Phe-$β^3$Lys)$_3$, $β^3$Tyr-($β^3$Val-$β^3$Val-$β^3$Lys)$_3$, $β^3$Tyr-(ACHC-ACHC-$β^3$Lys)$_3$, (ACHC-$β^3$Val-$β^3$Lys)$_3$, $β^3$Tyr-(ACHC-$β^3$Val-$β^3$Arg)$_3$, $β^3$Tyr-($β^3$Leu-ACHC-$β^3$Lys)$_3$ and C9-$β^3$Tyr-(ACHC-ACHC-$β^3$Lys)$_3$.

The invention further encompasses antifungal compositions that include an inhibitory amount of a β-peptide as described and claimed herein in combination with a pharmaceutically-acceptable carrier. The pharmaceutical composition can also be provided in the form of a kit, in combination with a delivery device.

The β-peptides described and claimed herein are envisioned to have wide utility including, but not limited to, use as an antifungal coating for implantable medical articles such as, for example, a stent, valve, pacemaker, defibrillator, artificial joint, prosthesis, neurostimulator, ventricular assist device, congestive heart failure device, indwelling catheter, insulin pump, incontinence device, cochlear device, or embolic filter.

These and other features and advantages of various exemplary embodiments of the methods according to this invention are described, or are apparent from, the following detailed description of various exemplary embodiments of the methods according to this invention.

BRIEF DESCRIPTION OF THE FIGURES

Various exemplary embodiments of the methods of this invention will be described in detail, with reference to the following figures.

FIG. 1. Comparative data demonstrating cecropin B and magainin peptides are not active against *Candida albicans*.

FIG. 5. Effect of oligomer length on MIC for ACHC-$β^3$Val-$β^3$Lys series β-peptides.

FIG. 6. Effect of N-terminal $β^3$Tyr on MIC for various β-peptides.

FIG. 9. MIC data for amphiphilic versus scrambled β-peptides that demonstrates scrambled oligomers did not exhibit antifungal properties.

FIG. 10. The effect of varying side chain on MIC for various β-peptides.

FIG. 11. Antifungal activity is maintained when a conservative substitution is made at a $β^3$Lys residue.

FIG. 12. The effect on antifungal activity by incorporating differing ACHC enantiomers.

FIG. 17. Growth reduction of *C. albicans* strains by β-peptide treatment as observed in biofilm susceptibility assay.

FIG. 18. MIC data from planktonic testing of amphiphilic sequence isomers.

FIG. 19. MIC data from planktonic testing of enantiomers demonstrating similar activity.

FIG. 20. MIC data from planktonic testing demonstrating effect of peptide charge on antifungal activity.

FIG. 22. Summary of planktonic MIC and hemolysis results in tabular form.

DETAILED DESCRIPTION OF THE INVENTION

Figure 2:
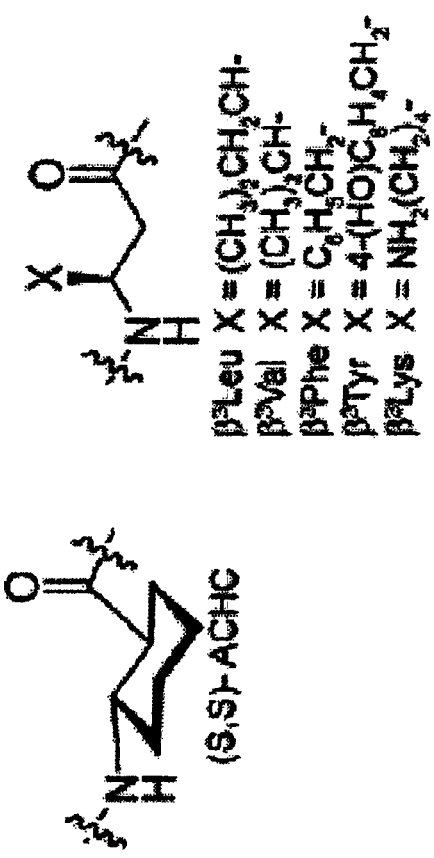
FIG. 2. Chemical structures of (S,S)-ACHC and various β-peptide residues.

In certain embodiments, the present invention provides β-peptides that function as antifungal agents under conditions that render host-defense α-peptides inactive against fungal pathogens. As an exemplary illustration of this invention's utility, the inventors focused on *Candida albicans*, the most prevalent fungal pathogen in humans. As described below, minimum inhibitory concentrations (MIC) were evaluated with three *C. albicans* strains using procedures suggested by the Clinical and Laboratory Standards Institute (formerly known as the National Committee for Clinical Laboratory Standards, NCCLS) (see Table 1); little difference was observed among the three strains which indicates the robustness of the invention. The minimum fungicidal concentrations (MFC) for these *C. albicans* strains were assessed using a colony-forming assay. In every case the MFC was equivalent to the MIC (data not shown).

TABLE 1

Average minimum inhibitory concentrations (MIC) against
*C. albicans* and percent hemolysis at the average MIC.

| Peptide | Average MIC | % Hemolysis at MIC |
|---|---|---|
| L-Magainin 2 derivative | >128 | 48 |
| D-Magainin 2 derivative | >128 | 48 |
| $β^3$Tyr-(ACHC-$β^3$Val-$β^3$Lys)$_3$ (1) | 16 | 21 |
| $β^3$Tyr-(ACHC-$β^3$Leu-$β^3$Lys)$_3$ (2) | 11 | 73 |
| $β^3$Tyr-(ACHC-$β^3$Phe-$β^3$Lys)$_3$ (3) | 8 | 80 |
| $β^3$Tyr-($β^3$Val-$β^3$Val-$β^3$Lys)$_3$ (4) | 69 | 9 |
| $β^3$Tyr-(ACHC-ACHC-$β^3$Lys)$_3$ (5) | 21 | 7 |
| (ACHC-$β^3$Val-$β^3$Lys)$_3$ (6) | 17 | 5 |
| $β^3$Lys-$β^3$Val-$β^3$Val-ACHC-$β^3$Lys-$β^3$Val-ACHC-ACHC-$β^3$Lys (7) | >128 | ND |

The two α-peptide sequences were initially evaluated to gauge the antifungal activities of amphiphilic host-defense peptides in the NCCLS assay, which was performed at pH 7 and physiological ionic strength. Previous reports indicated that the activities of cecropins and magainins against *C. albicans* depend sensitively on assay conditions. Referring to FIG. 1, at low ionic strength, such α-peptides inhibited growth above 10 μgrams/ml at pH 5.5, but were relatively inactive at pH 7.4. At pH 7, magainin 2 reduced *C. albicans* growth by 50% at concentrations below 1 μg/ml in low ionic strength solutions but was inactive at physiologic ionic strength.

The inventors determined that neither cecropin B nor a magainin derivative displays any activity under the NCCLS assay conditions (the latter peptide, a triple mutant of magainin 2, has been widely employed because of its enhanced antibacterial activity relative to magainin 2 itself). To determine whether the α-peptide inactivity observed arises from proteolytic degradation, the enantiomer of the magainin derivative was examined. Enantiomeric host-defense peptides retain the antibacterial activity of their natural antipodes, presumably because the mechanism of action involves bacterial membrane disruption rather than binding to a specific bacterial protein. The enantiomeric magainin derivative should resist protease attack, but this peptide was inactive in the NCCLS antifungal susceptibility assay.

The inventors then examined β-peptides intended to adopt 14-helical secondary structure (defined by 14-membered ring H-bonds formed between backbone C=O(i) and H—N(i-2) groups). Since the mechanism of antimicrobial activity appears to involve membrane disruption, it is critical to examine the susceptibility of host cell membranes, e.g., from human red blood cells, for comparison with activity against a eukaryotic microbe such as $C.$ $albicans$. In this example, the inventors focused on sequences containing trans-2-aminocyclohexanecarboxylic acid (ACHC) residues, which have a much higher 14-helical propensity than β-amino acid residues bearing a side chain adjacent to the nitrogen atom ($\beta^3$-residues). The corresponding chemical structures referred to by the terms ACHC, $\beta^3$Tyr, $\beta^3$Val, $\beta^3$Lys, $\beta^3$Leu and $\beta^3$Phe are depicted in FIG. 2.

Figure 3:
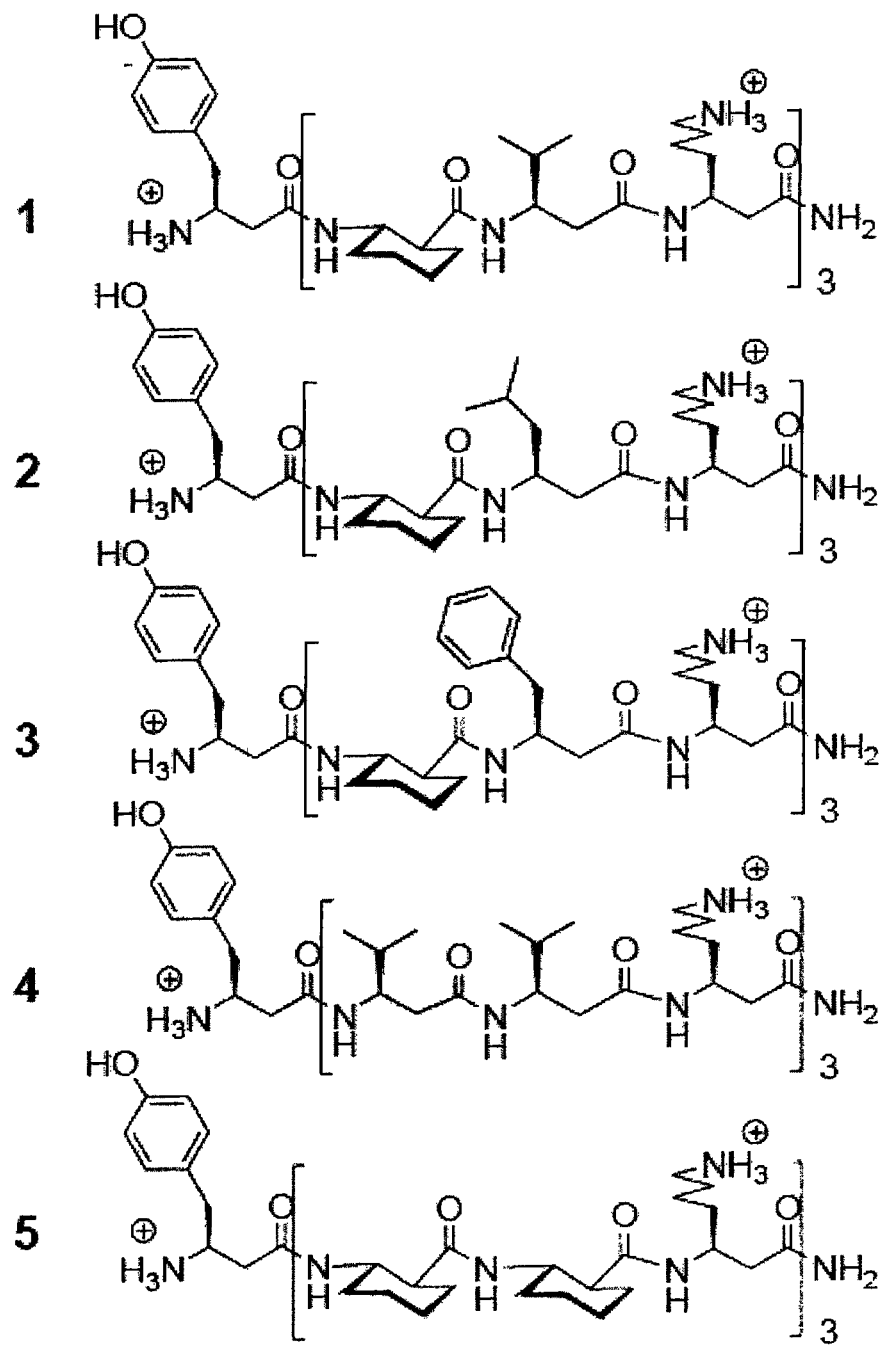
FIG. 3. β-Peptides analyzed by circular dichroism.
Figure 4:
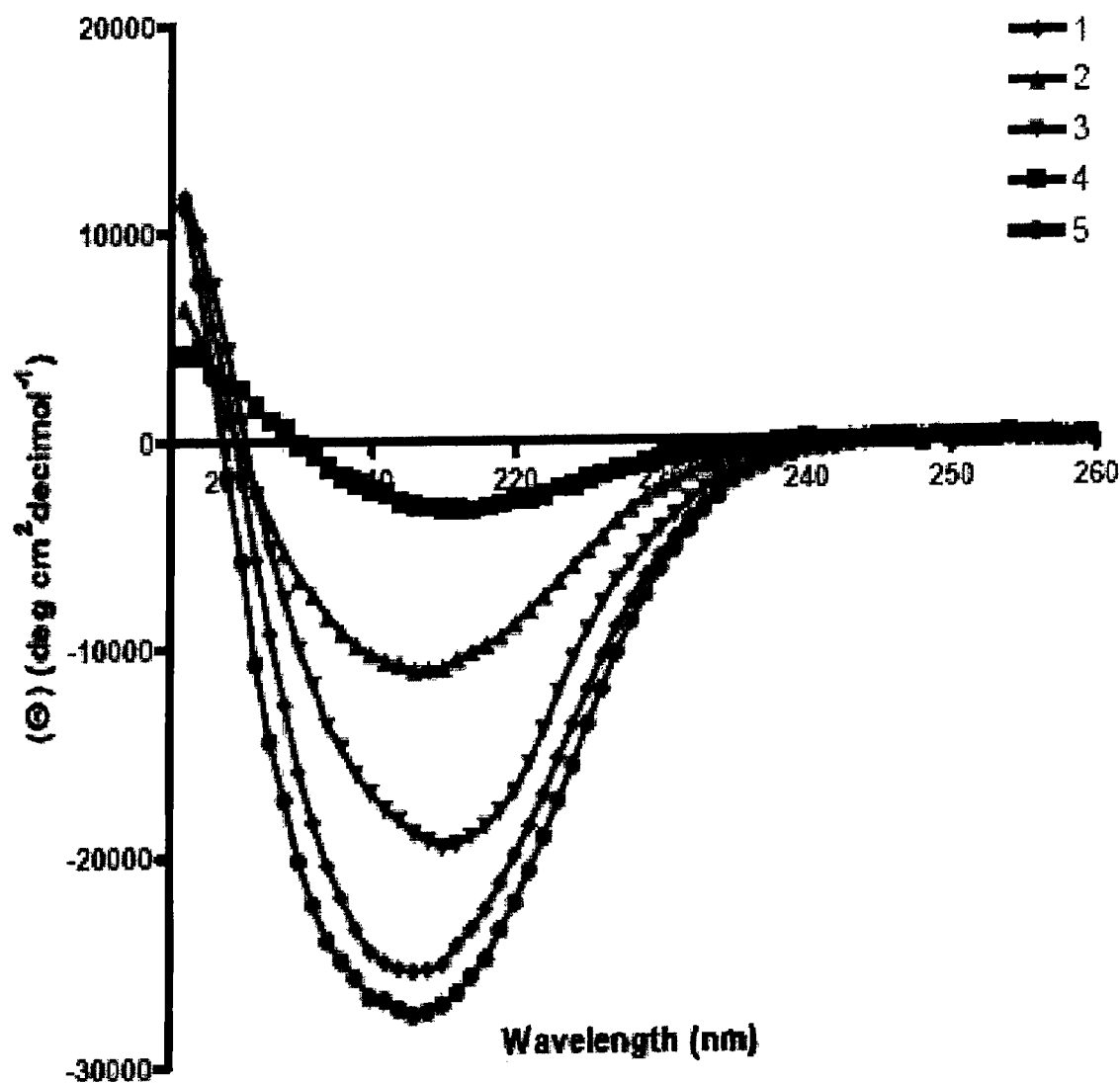
FIG. 4. Circular dichroism data for β-peptides (1-5) (100 μM) at 25° C. in 10 mM TRIS (pH 7.3). β-Peptides containing three or more ACHC residues, (1), (2), (3), and (5), have intense 14-helical signatures characterized by a minimum around 214 nm, whereas (4), which lacks ACHC, has only a weak 14-helical signature.

Surprisingly, significant antifungal activity has been identified for 14-helical β-peptides, given the lack of activity observed for the host defense α-peptides (see Table 1 and FIG. 3). The decamer $\beta^3$Tyr-(ACHC-$\beta^3$Val-$\beta^3$Lys)$_3$ (1) displayed a reasonably low MIC (16 μg/ml) and only a moderate degree of hemolysis at the MIC (21%). The 14-helix has approximately three residues per turn; therefore, the triad repeat in this deca-β-peptide should generate a globally amphiphilic structure in which the hydrophobic ACHC and $\beta^3$Val residues are clustered on one side of the helix and the cationic $\beta^3$Lys residues are clustered on the other side. The N-terminal $\beta^3$Tyr residue was included to aid absorbance-based concentration determination.

β-peptides (2-5), analogues of (1) denoted in Table 1 and shown in FIG. 3, were evaluated to elucidate relationships among sequence, folding and antifungal and hemolytic activities. As shown in FIG. 4, circular dichroism (CD) in aqueous buffer indicated that each of the ACHC-containing β-peptides has a substantial 14-helical population (5>1>3>2), while, as expected, little or no 14-helicity is evident for (4), which contains exclusively $\beta^3$-residues. The fact that (4) displays substantially weaker antifungal activity than do analogues (1-3) and (5) suggests that 14-helical folding is important for this activity. However, neither antifungal nor hemolytic activity is directly correlated with the order of 14-helical folding indicated by the CD data, which suggests that the biological activities are determined by an interplay among conformational propensity and other physicochemical properties such as net hydrophobicity. The decamer length appears to be optimal, since no antifungal activity could be detected when (1) was truncated or extended by one ACHC-$\beta^3$Val-$\beta^3$Lys triad (see FIG. 5, e.g., where the effect of length on MIC in the ACHC-$\beta^3$Val-$\beta^3$Lys series 0 peptides is provided for comparative purposes).

Previous work with β-peptides closely related to (1) revealed that removal of the N-terminal $\beta^3$Tyr residue decreased hemolytic activity without diminishing antibacterial activity. As shown in FIG. 6, the inventors identified a similar, but yet unexpected, effect in terms of antifungal activity and selectivity, as indicated by the behavior of (ACHC-$\beta^3$Val-$\beta^3$Lys)$_3$ (6): the average MIC is indistinguishable relative to $\beta^3$Tyr-containing variant (1), but without the $\beta^3$Tyr only 5% hemolysis occurs at the MIC.

Figure 7:
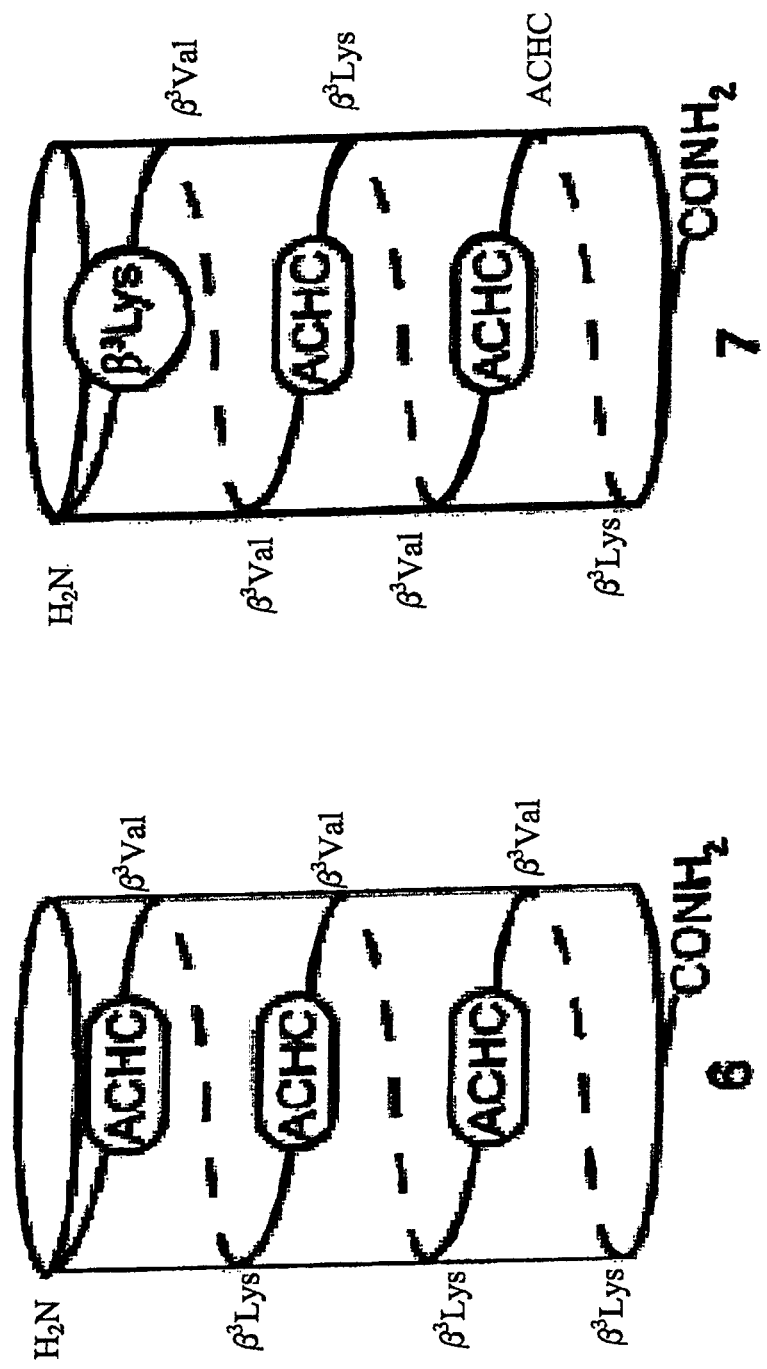
FIG. 7. Three-dimensional representation of facially amphiphilic and non-amphiphilic 14-helical β-peptides (6) and (7).
Figure 8:
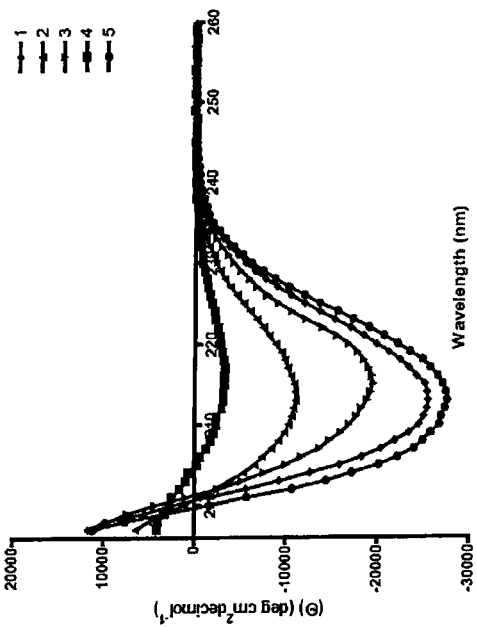
FIG. 8. The effect of 14-helical conformation on MIC for various β-peptides.

The importance of 14-helical folding for antifungal activity is shown by the dramatic contrast between (6) and sequence isomer $\beta^3$Lys-$\beta^3$Val-$\beta^3$Val-ACHC-$\beta^3$Lys-$\beta^3$Val-ACHC-ACHC-$\beta^3$Lys (7). The 14-helical conformation available to (7) is not globally amphiphilic, because the cationic $\beta^3$Lys residues are distributed around the helix circumference rather than aligned along one side, as depicted in FIG. 7. FIG. 8 further illustrates the relationship of the 14 helical conformation relative to observed MIC.

Referring now to FIG. 9 and Table 1, it is seen that analogous "scrambled" β-peptide sequence isomers are completely inactive against $C.$ $albicans$, which is consistent with the lack of antifungal activity reported herein for scrambled peptides including β-peptide 7.

Referring to FIG. 10, the effect on MIC of varying side chain groups can be seen. A series of substitutions at the $\beta^3$Val residue in the decamer $\beta^3$Tyr-(ACHC-$\beta^3$Val-$\beta^3$Lys)$_3$ with ACHC, $\beta^3$Leu and $\beta^3$Phe residues yielded oligomers having comparable MIC values. However, substitution of the $\beta^3$Val residue with a $\beta^3$Lys residue yielded an oligomer having a substantially higher MIC value. FIG. 11 depicts data wherein the $\beta^3$Lys in the decamer $\beta^3$Tyr-(ACHC-$\beta^3$Val-$\beta^3$Lys)$_3$ is substituted with a $\beta^3$Arg residue. This substitution provided an oligomer possessing comparable MIC values to the parent oligomer.

Differing ACHC enantiomers were incorporated within the decamer $\beta^3$Tyr-(ACHC-$\beta^3$Val-$\beta^3$Lys)$_3$ to examine the effect on MIC. FIG. 12 illustrates the MIC values obtained where the ACHC residue, previously in the S, S enantiomer conformation, was substituted with an ACHC residue in the R, R conformation to create a diastereomer of β-peptide (1). The MIC values obtained for the substituted oligomer were significantly higher than those for the comparable parent oligomer. Therefore, appropriate stereochemistry is an additional factor in the design of antifungal β-peptides according to the invention.

Figure 13:
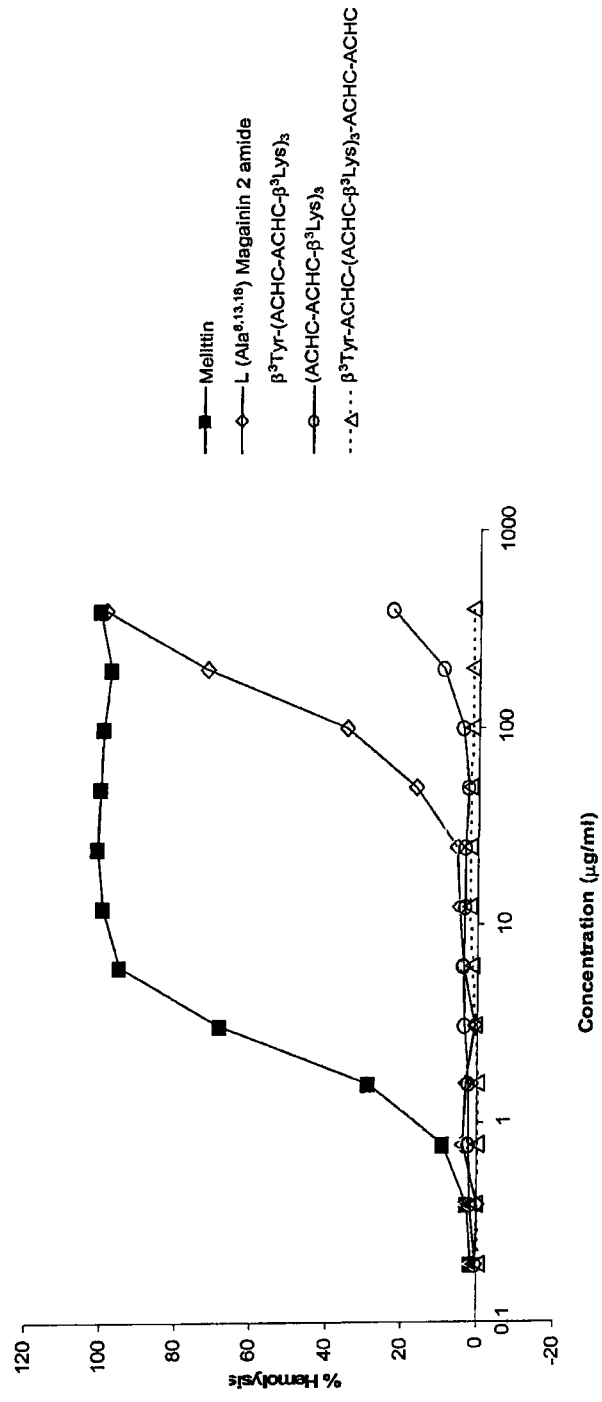
FIG. 13. Hemolysis activity for melittin, L magainin 2 amide, and ACHC-ACHC-$β^3$Lys series β-peptides.
Figure 14:
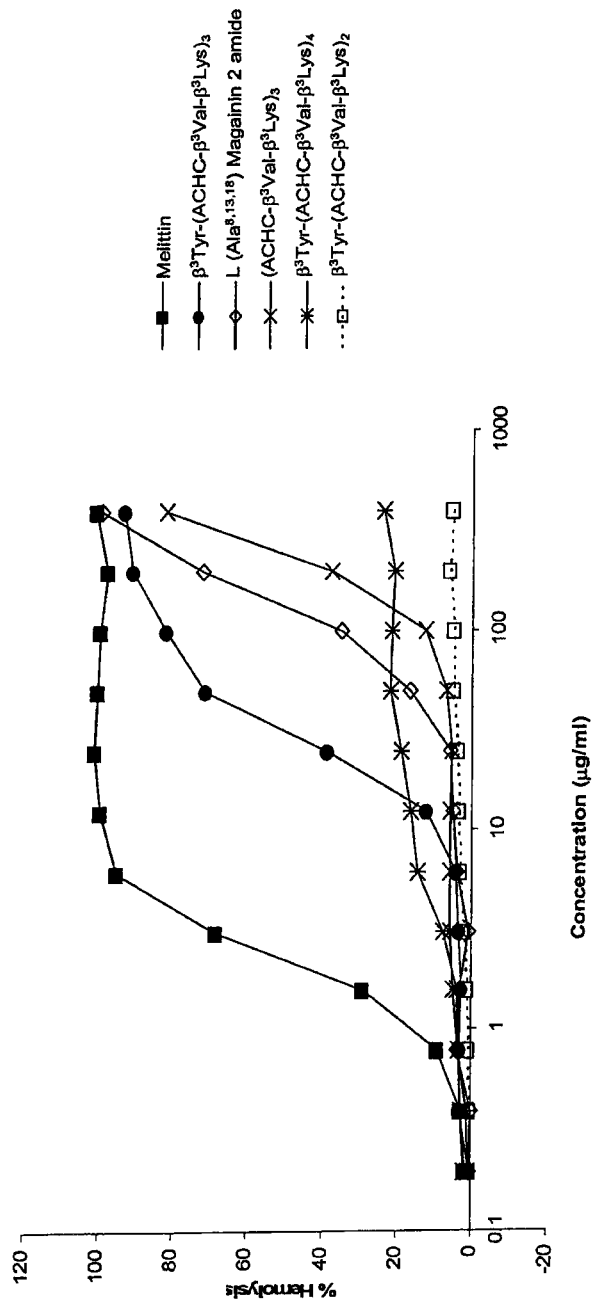
FIG. 14. Hemolysis activity for melittin, L magainin 2 amides, and ACHC-$β^3$Val-$β^3$Lys series β-peptides.
Figure 15:
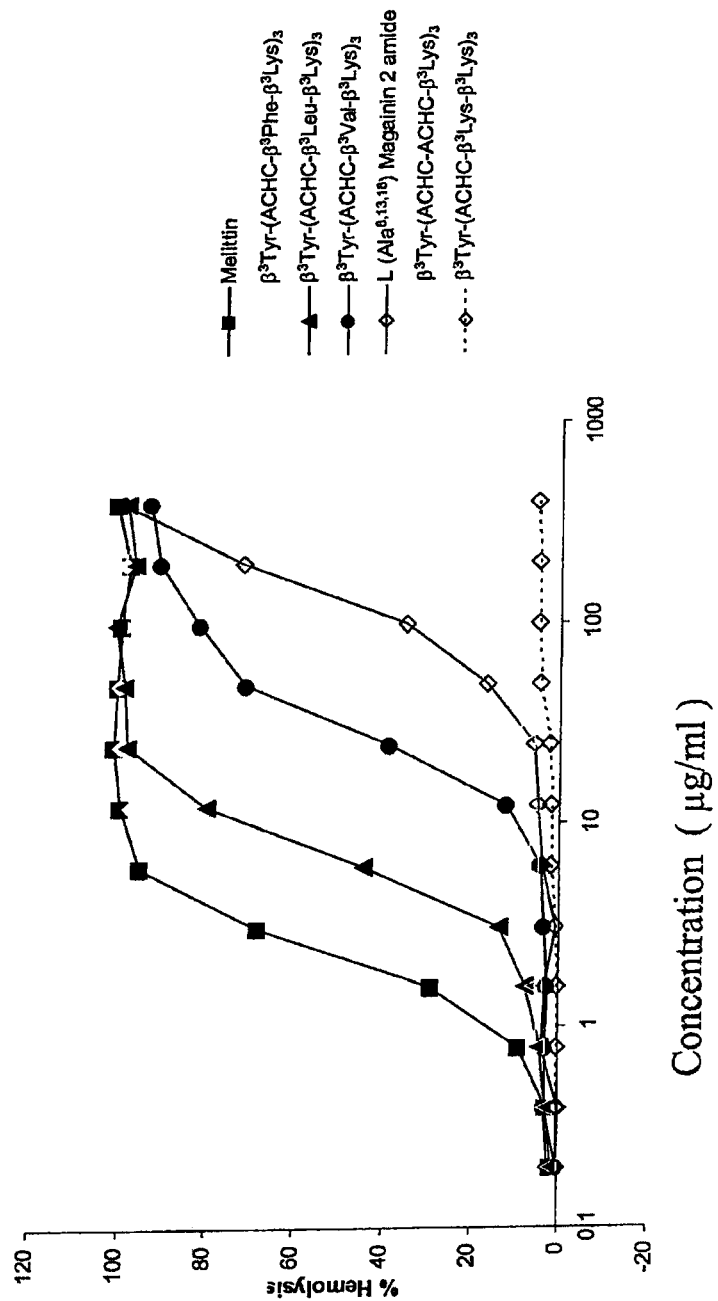
FIG. 15. Hemolysis activity for melittin, L magainin 2 amides, and ACHC—X-$β^3$Lys series β-peptides.
Figure 16:
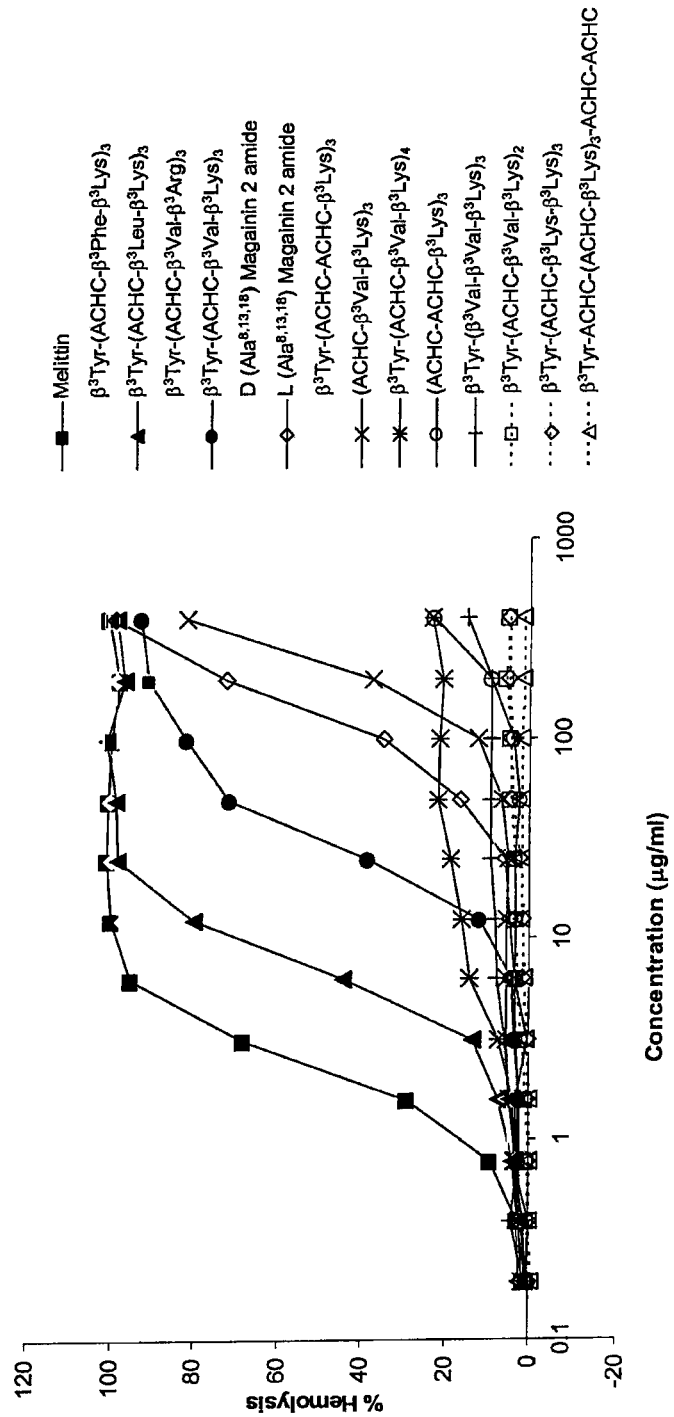
FIG. 16. Combined depiction of hemolysis activity for the α and β-peptides separately shown in FIGS. 13-15.
Figure 21:
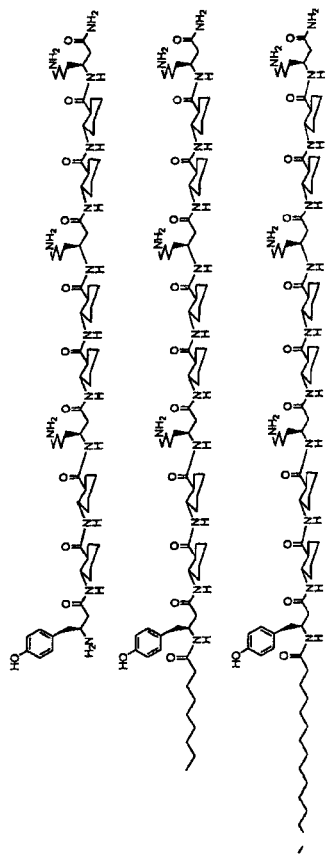
FIG. 21. MIC data from planktonic testing showing effect of acylation of peptide on antifungal activity.

As can be appreciated, β-peptides according to the invention display notably low hemolytic activities. Table 1 provides data substantiating this observation and, in addition, FIGS. 13, 14 and 15 further illustrate the hemolytic properties of β-peptides including, but not limited to, ACHC-ACHC-$\beta^3$Lys, ACHC-$\beta^3$Val-$\beta^3$Lys, ACHC-$\beta^3$Leu-$\beta^3$Lys, ACHC-$\beta^3$Phe-$\beta^3$Lys peptides of varying length (2-4 triad repeats). β-peptides as taught herein performed more favorably in hemolysis assays than did melittin, and, in some cases, more favorably than did D and L triple mutant magainin 2 amides. FIG. 16 provides a comprehensive illustration of hemolytic activities for et and β-peptides examined in the presently-described study.

Figure 17:
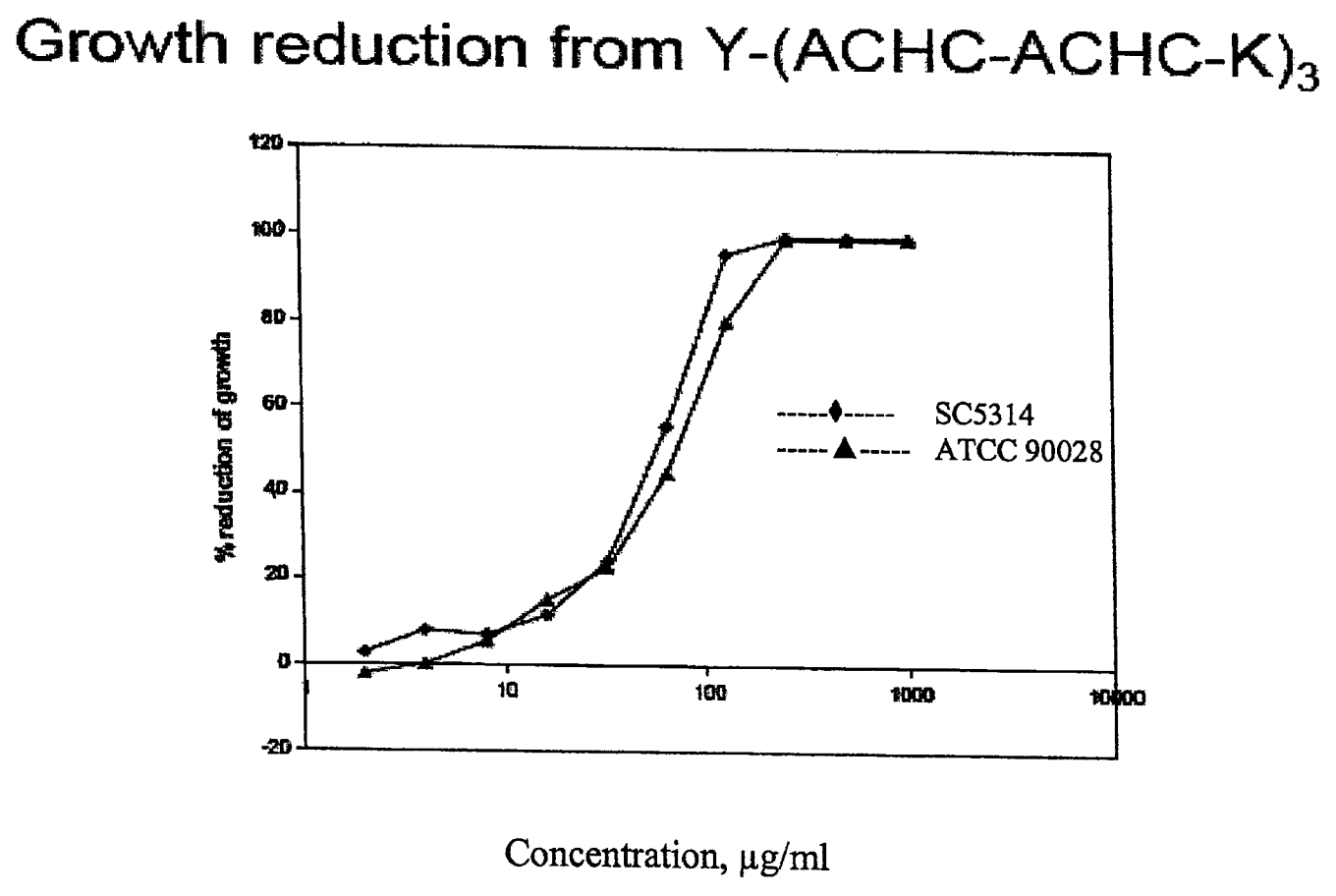

The decamer $\beta^3$Tyr-(ACHC-ACHC-$\beta^3$Lys)$_3$ was further assayed for its ability to inhibit fungal growth of two $C.$ $albican$ strains in the context of a biofilm environment. The biofilm assay better approximates physiological conditions relating to systemic candidemia as compared to standard liquid assays. The data provided in FIG. 17 demonstrate that the assayed decamer was effective at reducing fungal growth at near 100% when contacted with the biofilm at concentrations of 75-100 μg/mL. Accordingly, it can be appreciated that the present invention has demonstrated utility under conditions approximating certain clinical settings.

Two amphiphilic sequence isomers, $\beta^3$Tyr-(ACHC-$\beta^3$Leu-$\beta^3$Lys)$_3$ and $\beta^3$Tyr-($\beta^3$Leu-ACHC-$\beta^3$Lys)$_3$, were tested by the inventors for their antifungal activity against planktonic $C.$ $albicans$ strain SC5314. As depicted in FIG. 18, $\beta^3$Tyr-(ACHC-$\beta^3$Leu-$\beta^3$Lys)$_3$ had an MIC of 82 g/mL and $\beta^3$Tyr-($\beta^3$Leu-ACHC-$\beta^3$Lys)$_3$ had an MIC of 16 μg/mL. The similar activity of the isomers shows that the sequence of residues can be changed without producing a large change in antifungal activity. Two amphiphilic isomers composed of stereoisomers of β-amino acids were also tested with corresponding results shown in FIG. 19. As expected for peptides that act via a general membrane disruption mechanism, (R)β³Tyr-[(R,R)ACHC—(R)β³Phe-(R)β³Lys]$_3$ and (S)β³Tyr-[(S,S)ACHC—(S)β³Phe-(S)β³Lys]$_3$ had identical MIC of 8 µg/mL against all tested strains.

β³Tyr-(ACHC-ACHC-β³Lys)$_3$, with a charge of +4 and an MIC of 16 µg/mL against SC5314, was used as a starting point to evaluate changes in the charge of the β-peptides. By exchanging negatively-charged β³Glu residues for the positively-charged β³Lys in the β-peptide, the overall β-peptide charge became −2 and antifungal activity was eliminated (MIC>128 µg/mL) (FIG. 20). Likewise, substitution of a single β³Glu for the β³Lys at position 4 or 7 decreased the overall charge of the β-peptide to +2 and also resulted in loss of antifungal activity (MIC>128/µg/mL).

To further demonstrate the present invention's breadth, various useful terminal-modified versions of the above-described peptides were constructed. β³Tyr-(ACHC-ACHC-β³Lys)$_3$ (MIC average=21 µg/mL) was acylated by coupling nonanoic acid [C9-β³Tyr-(ACHC-ACHC-β³Lys)$_3$] or pentadecanoic acid [C15-β³Tyr-(ACHC-ACHC-β³Lys)$_3$] to the N-terminus. As shown in FIG. 20, C15-β³Tyr-(ACHC-ACHC-β³Lys)$_3$ was not active (MIC>128 µg/mL), but C9-β³Tyr-(ACHC-ACHC-β³Lys)$_3$ had activity very similar to the parent compound, with an average MIC of 16 µg/mL.

The acylated β-peptide results demonstrate the activity of antifungal β-peptides is maintained after tethering to a second, diverse molecule. Accordingly, the present invention contemplates various modifications to the presently described peptides which direct delivery of the anti-fungal agents to pre-selected cell/tissue targets. Various modifications are known to the artisan and include, but are not limited to, tethering to membrane targeting moieties such as long chain acyl groups or phosphonium ions.

Figure 23:
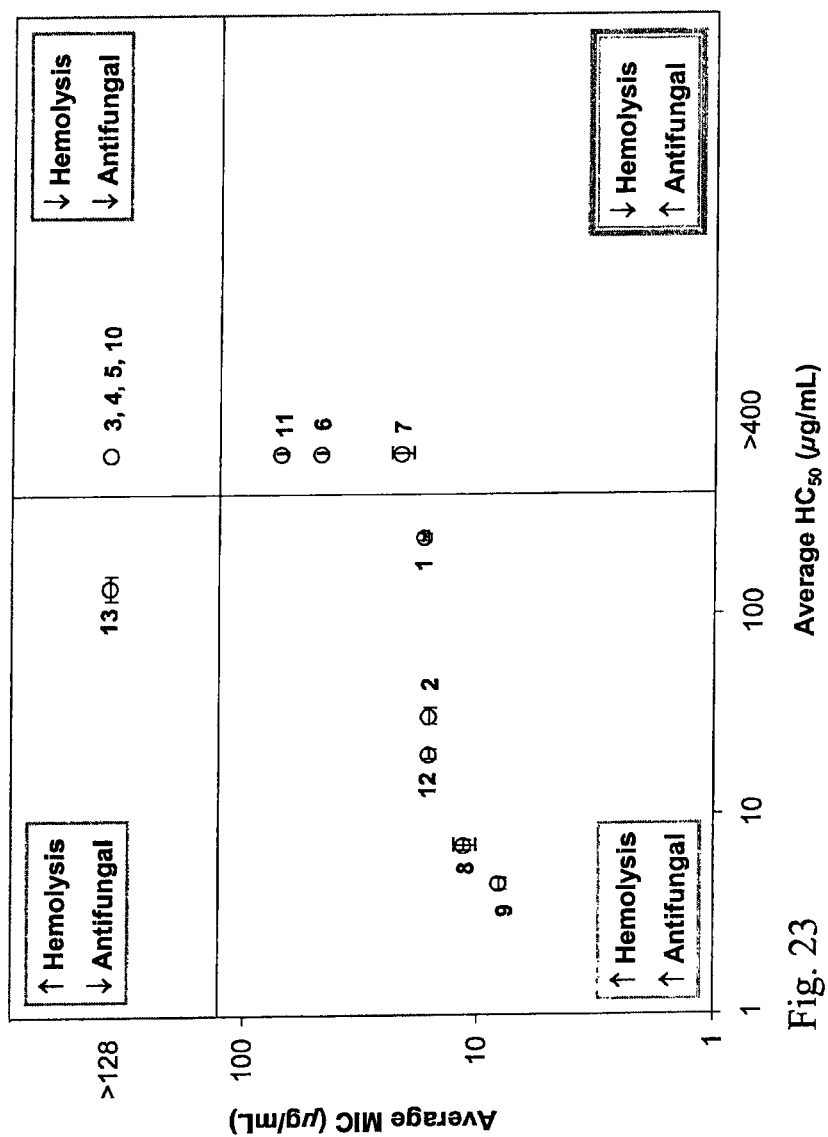
FIG. 23. Summary of planktonic MIC and hemolysis results in graphic form.

As can be appreciated, the present β-peptides have activity at least comparable to the activity of prior antifungals in the assay for antifungal activity against planktonic cells. The MIC range for the active β-peptides is 4.1-72.9 µM, with many of the β-peptides having MIC below 10 µM. Amphotericin B has an MIC range of 0.3-2.2 µM, and fluconazole has an MIC range of 0.8-3.3 µM, though resistance of fungi to azole drugs can render azoles ineffective at concentrations much higher than these. (National Committee for Clinical Laboratory Standards *Reference method for broth dilution antifungal susceptibility testing of yeasts: approved standard—second edition*; NCCLS document M27-A2; NCCLS: Wayne, Pa., 2002). FIGS. 22 and 23 depict summaries of planktonic MIC and hemolysis results in table and graphic presentation, respectively.

Figure 24:
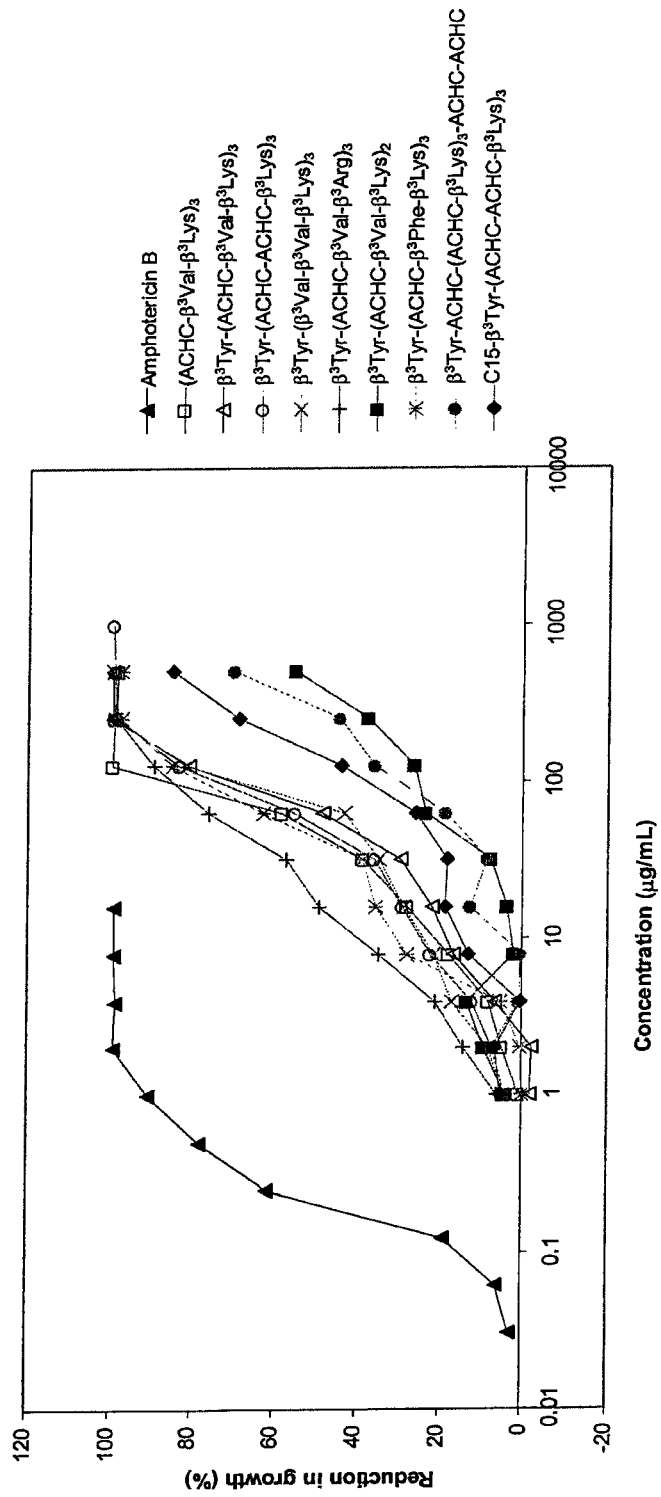
FIG. 24. Summary of peptide activity against ATCC 90028 biofilm.

The ability of β-peptides to kill *C. albicans* cells in biofilms was also evaluated. Biofilms of SC5314, ATCC 24433, and ATCC 90028 were grown in wells of 96-well plates and then incubated with β-peptide. When tested in the biofilm assay, β-peptides that showed activity in the planktonic assay [(ACHC-β³Val-β³Lys)$_3$, β³Tyr-(ACHC-β³Val-β³Lys)$_3$, β³Tyr-(ACHC-ACHC-β³Lys)$_3$, β³Tyr-(β³Val-β³Val-β³Lys)$_3$, β³Tyr-(ACHC-β³Val-β³Arg)$_3$, and β³Tyr-(ACHC-β³Phe-β³Lys)$_3$] reduced biofilms by 80% compared to untreated biofilms at concentrations about 1-15 times their planktonic MIC. See FIG. 24 for a graphic depiction of the data described in this paragraph. Concentrations of 128-256 µg/mL for the these β-peptides killed nearly all cells in the biofilms.

In contrast, β-peptides lacking activity in the planktonic assay [β³Tyr-ACHC-(ACHC-β³Lys)$_3$-ACHC-ACHC, C15-β³Tyr-(ACHC-ACHC-β³Lys)$_3$, and β³Tyr-(ACHC-β³Val-β³Lys)$_2$] showed low activity in the biofilm killing assay. The non-amphiphilic β-peptide β³Tyr-ACHC-(ACHC-β³Lys)$_3$-ACHC-ACHC and the short β-peptide β³Tyr-(ACHC-β³Val-β³Lys)$_2$ never reached 80% reduction in biofilm growth at the highest concentration tested, and the acylated β-peptide C15-β³Tyr-(ACHC-ACHC-13 Lys)$_3$ barely surpassed this mark.

Figure 25:
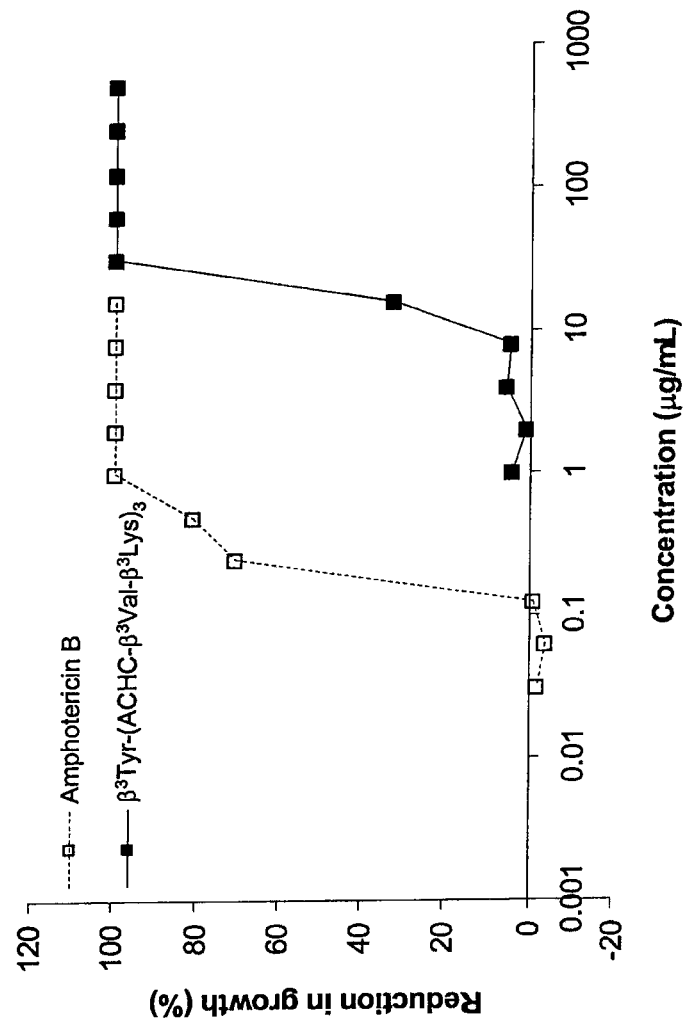
FIG. 25. Prevention of biofilm formation by β-peptides.
Figure 26:
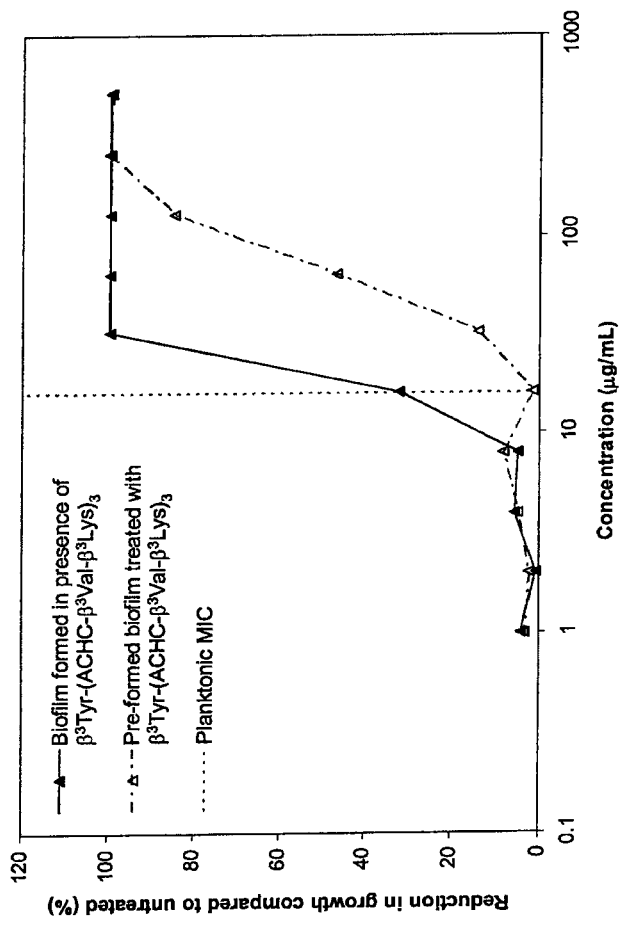
FIG. 26. Presence of beta-peptides prevents biofilm formation at concentrations lower than those required to kill preformed biofilms.

The ability of a β-peptide to prevent the formation of *C. albicans* biofilms was also investigated and relevant results are shown in FIG. 25. *C. albicans* SC5314 cells at the same density used in testing pre-formed biofilms were incubated with a β-peptide, and the resulting biofilm growth was evaluated. As depicted in FIG. 26, β³Tyr-(ACHC-β³Val-β³Lys)$_3$ completely prevented biofilm formation at 32 µg/mL, a concentration much lower than the 256 µg/mL needed to kill pre-formed biofilms and only two times its planktonic MIC.

The ability of the present β-peptides to prevent the formation of biofilms is useful in applications in material coatings to prevent infections associated with biofilm growth on a medical device including, but not limited to, stent, valve, pacemaker, defibrillator, artificial joint, prosthesis, neurostimulator, ventricular assist device, congestive heart failure device, indwelling catheter, insulin pump, incontinence device, cochlear device, or embolic filter. As defined herein, a "fungal-resistant" medical article means an article coated with β-peptides of the present invention so as to prevent the statistically-significant formation of biofilms. The coating process may be accomplished by any methodology for coating known to the artisan, including dipping or spraying followed by drying to provide a deposited layer of β-peptide on the respective article.

The results described in the present disclosure demonstrate that unnatural foldamers can display significant antifungal activity. The present findings are significant because they identify a new class of antifungal agents that, by virtue of modular structure, can be modified by methodology known in the field to generate a wide variety of useful antifungal agents. It can be appreciated that the present inventors have demonstrated antifungal activity of β-peptides under conditions (pH 7, physiological ionic strength) that do not support host-defense amphiphilic α-peptide activity.

Terminology in this disclosure related to β-peptides, particularly β³ and β² residues, is as defined by Cheng and coworkers (*Chem. Rev.* 2001, 101, 3219-3232; incorporated herein by reference). As used herein, the term "hydrophobic residue" shall refer to β-amino acid residues bearing hydrophobic side chains; these residues include but are not limited to, β³Val, β³Phe, β³Ile, β³Ala, β³Leu, β²Val, β²Phe, β²Ile, β²Ala, and β²Leu, all of which have side chains found in α-amino acid residues in natural proteins. β-Amino acid residues with other "non-natural" hydrophobic side chains, such as ethyl, n-propyl or n-butyl side chains, are also included within the scope of the term "hydrophobic residue."

The term "hydrophobic residue" shall further encompass certain β-peptide residues having constrained backbones including, but not limited to, cyclohexane derivatives such as trans-2-aminocyclohexanecarboxylic acid (ACHC) or cyclopentane derivatives such as trans-2-aminocyclopentanecarboxylic acid. The term "cationic residue" shall refer to β-amino acid residues bearing natural or non-natural side chains that bear a positive charge under physiological conditions, including, but not limited to, β³Lys, β³Arg, β³His, β³Orn, and the β² variants of these residues.

Within a particular β-peptide, hydrophobic and cationic residues are independently selected such that the residues form triads having the sequential pattern hydrophobic-hydrophobic-cationic, hydrophobic-cationic-hydrophobic, or cationic-hydrophobic-hydrophobic. The sequential pattern is repeated within the β-peptide to yield a molecule that is globally amphiphilic. In certain embodiments, the triads may be identical to one another with respect to the exact residues making up the triads, as is illustrated by the molecule (ACHC-β³Val-β³Lys)₃. However, the exact identity of the residues forming each triad need not be shared between triads within a single β-peptide but may vary so long as the sequential pattern of hydrophobic residues to cationic residues is maintained within the β-peptide.

In certain embodiments, β-peptides according to the invention may be modified at their N- and/or C-terminus by various end-capping methodologies known in the art. For example, acetylation of the N-terminus can be accomplished by reacting the final peptide with acetic anhydride before cleavage from a resin. The C terminus may be modified by standard methods through the choice of resin linker, such as by using a benzyl hydrylamine (carboxamide) or hydroxybenzyl linker (carboxylic acid). Additional N-terminus modifications include, but are not limited to, protecting groups such as Boc or Cbz, and also acyl groups such as, e.g., propanoyl, butanoyl, pentanoyl, nonanoic acid, or pentadecanoic acid (see examples herein). Additional C-terminus modifications include, but are not limited to, N-alkyl or N-aryl or N,N-dialkyl or N,N-diaryl amides and esters.

Accordingly, the present invention provides methods for inhibiting fungal growth. Such methods include the step of contacting a fungus to be inhibited with an inhibitory amount of a β-peptide. Such β-peptides preferably have the structure:

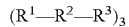

(R¹—R²—R³)₃ wherein R¹, R², and R³ of each triad are independently selected from β-amino acid residues bearing hydrophobic and cationic side chains such that the R¹—R²—R³ triads in the β-peptide consist of β-amino acid residues bearing hydrophobic and cationic side chains in the sequential pattern hydrophobic-hydrophobic-cationic, hydrophobic-cationic-hydrophobic, or cationic-hydrophobic-hydrophobic.

To further facilitate formation of globally amphiphilic peptides, the 3-amino acid residues are homo-chiral. Certain preferred β-peptides for use in the method include, but are not limited to, (ACHC-β³Val-β³Lys)₃, β³Tyr-(ACHC-β³Val-β³Lys)₃, β³Tyr-(ACHC-β³Leu-β³Lys)₃, β³Tyr-(ACHC-β³Phe-β³Lys)₃, β³Tyr-(β³Val-β³Val-β³Lys)₃, β³Tyr-(ACHC-ACHC-β³Lys)₃, (ACHC-β³Val-β³Lys)₃, β³Tyr-(ACHC-β³Val-β³Arg)₃, β³Tyr-(β³Leu-ACHC-β³Lys)₃ and C9-β³Tyr-(ACHC-ACHC-β³Lys)₃, or combinations thereof.

In yet another embodiment, the invention encompasses particular β-peptides possessing antifungal activities. Such compounds have the structure:

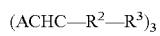

(ACHC—R²—R³)₃ wherein R² is β³Val, β³Leu or β³Phe, and R³ is β³Lys or β³Arg. These β-peptides may, alternatively, include a terminus capping group, e.g., a β³Tyr residue at their N-terminus. It is further preferred that the β-amino acid residues are homo-chiral, most preferably in S conformation.

In another aspect, the invention encompasses preparation and use of medicaments and pharmaceutical compositions comprising a compound described herein as an active ingredient. The following definitions are provided in view of such applications.

"Subject" means mammals and non-mammals. "Mammals" means any member of the class Mammalia including, but not limited to, humans, non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

A "pharmaceutically acceptable carrier" as used herein means a chemical composition with which a biologically active ingredient can be combined and which, following the combination, can be used to administer the active ingredient to a subject.

A "pharmaceutically acceptable" ester or salt as used herein means an ester or salt form of the active ingredient which is compatible with any other ingredients of the pharmaceutical composition and which is not deleterious to the subject to which the composition is to be administered. The terms "pharmaceutically acceptable salts" or "pro-drugs" includes the salts and prodrugs of compounds that are, within the scope of sound medical judgment, suitable for use with patients without undue toxicity, irritation, allergic response, and the like, commensurate with a reasonable benefit/risk ratio, and effective for their intended use, as well as the zwitterionic forms, where possible, of the compounds.

The term "salts" refers to inorganic and organic salts of compounds. These salts can be prepared in situ during the final isolation and purification of a compound, or by separately reacting a purified compound with a suitable organic or inorganic acid or base, as appropriate, and isolating the salt thus formed. Representative salts include the hydrobromide, hydrochloride, sulfate, bisulfate, nitrate, acetate, oxalate, palmitate, stearate, laurate, borate, benzoate, lactate, phosphate, tosylate, besylate, esylate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Compounds having N-oxides of amino groups, such as produced by reaction with hydrogen peroxide, are also encompassed.

A "therapeutically effective amount" means an amount of a compound that, when administered to a subject for treating a disease, is sufficient to effect such treatment for the disease. The "therapeutically effective amount" will vary depending on the compound, the disease state being treated, the severity or the disease treated, the age and relative health of the subject, the route and form of administration, the judgment of the attending medical or veterinary practitioner, and other factors.

For purposes of the present invention, "treating" or "treatment" describes the management and care of a patient for the purpose of combating the disease, condition, or disorder. The terms embrace both preventative, i.e., prophylactic, and palliative treatment. Treating includes the administration of a compound of present invention to prevent the onset of the symptoms or complications, alleviating the symptoms or complications, or eliminating the disease, condition, or disorder.

The form in which the active compound is administered to the fungal cell is not critical; the active compound need only reach the cell, directly or indirectly.

A compound is administered to a patient in a therapeutically effective amount. A compound can be administered alone or as part of a pharmaceutically acceptable composition. In addition, a compound or composition can be administered all at once, as for example, by a bolus injection, multiple times, such as by a series of tablets, or delivered substantially uniformly over a period of time, as for example, using transdermal delivery. It is also noted that the dose of the compound can be varied over time. A compound can be administered using an immediate release formulation, a controlled release formulation, or combinations thereof. The term "controlled release" includes sustained release, delayed release, and combinations thereof.

A pharmaceutical composition of the invention can be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a patient or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the human treated and further depending upon the route by which the composition is to be administered. By way of example, the composition can comprise between 0.1% and 100% (w/w) active ingredient. A unit dose of a pharmaceutical composition of the invention will generally comprise from about 100 milligrams to about two grams of the active ingredient, and preferably comprises from about 200 milligrams to about 1.0 gram of the active ingredient.

Another aspect of the invention relates to a kit comprising a pharmaceutical composition of the invention and instructional material. Instructional material includes a publication, a recording, a diagram, or any other medium of expression which is used to communicate the usefulness of the pharmaceutical composition of the invention for one of the purposes set forth herein in a human. The instructional material can also, for example, describe an appropriate dose of the pharmaceutical composition of the invention. The instructional material of the kit of the invention can, for example, be affixed to a container which contains a pharmaceutical composition of the invention or be shipped together with a container which contains the pharmaceutical composition. Alternatively, the instructional material can be shipped separately from the container with the intention that the instructional material and the pharmaceutical composition be used cooperatively by the recipient.

The invention also includes a kit comprising a pharmaceutical composition of the invention and a delivery device for delivering the composition to a human. By way of example, the delivery device can be a squeezable spray bottle, a metered-dose spray bottle, an aerosol spray device, an atomizer, a dry powder delivery device, a self-propelling solvent/powder-dispensing device, a syringe, a needle, a tampon, or a dosage-measuring container. The kit can further comprise an instructional material as described herein. The kit also comprises a container for the separate compositions, such as a divided bottle or a divided foil packet. Additional examples of containers include syringes, boxes, bags, and the like. Typically, a kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

It may be desirable to provide a memory aid on the kit, e.g., in the form of numbers next to the tablets or capsules whereby the numbers correspond with the days of the regimen that the tablets or capsules so specified should be ingested. Another example of such a memory aid is a calendar printed on the card, e.g., as follows "First Week, Monday, Tuesday, . . . etc. . . . Second Week, Monday, Tuesday," etc. Other variations of memory aids will be readily apparent. A "daily dose" can be a single tablet or capsule or several pills or capsules to be taken on a given day.

In another embodiment of the present invention, a dispenser designed to dispense the daily doses one at a time in the order of their intended use is provided. Preferably, the dispenser is equipped with a memory aid, so as to further facilitate compliance with the dosage regimen. An example of such a memory aid is a mechanical counter, which indicates the number of daily doses that have been dispensed. Another example of such a memory aid is a battery-powered microchip memory coupled with a liquid crystal readout, or audible reminder signal which, for example, reads out the date that the last daily dose has been taken and/or reminds one when the next dose is to be taken.

An antifungal composition, optionally comprising other pharmaceutically active compounds, can be administered to a patient either orally, rectally, parenterally, (for example, intravenously, intramuscularly, or subcutaneously) intracisternally, intravaginally, intraperitoneally, intravesically, locally (for example, powders, ointments or drops), or as a buccal or nasal spray. Other contemplated formulations include projected nanoparticles, liposomal preparations, resealed erythrocytes containing the active ingredient, and immunologically-based formulations.

Parenteral administration of a pharmaceutical composition includes any route of administration characterized by physical breaching of a tissue of a human and administration of the pharmaceutical composition through the breach in the tissue. Parenteral administration thus includes administration of a pharmaceutical composition by injection of the composition, by application of the composition through a surgical incision, by application of the composition through a tissue-penetrating non-surgical wound, and the like. In particular, parenteral administration includes subcutaneous, intraperitoneal, intravenous, intraarterial, intramuscular, or intrasternal injection and intravenous, intraarterial, or kidney dialytic infusion techniques.

Compositions suitable for parenteral injection comprise the active ingredient combined with a pharmaceutically acceptable carrier such as physiologically acceptable sterile aqueous or nonaqueous solutions, dispersions, suspensions, or emulsions, or may comprise sterile powders for reconstitution into sterile injectable solutions or dispersions. Examples of suitable aqueous and nonaqueous carriers, diluents, solvents, or vehicles include water, isotonic saline, ethanol, polyols (propylene glycol, polyethylene glycol, glycerol, and the like), suitable mixtures thereof, triglycerides, including vegetable oils such as olive oil, or injectable organic esters such as ethyl oleate. Proper fluidity can be maintained, for example, by the use of a coating such as lecithin, by the maintenance of the required particle size in the case of dispersions, and/or by the use of surfactants. Such formulations can be prepared, packaged, or sold in a form suitable for bolus administration or for continuous administration. Injectable formulations can be prepared, packaged, or sold in unit dosage form, such as in ampules, in multi-dose containers containing a preservative, or in single-use devices for auto-injection or injection by a medical practitioner.

Formulations for parenteral administration include suspensions, solutions, emulsions in oily or aqueous vehicles, pastes, and implantable sustained-release or biodegradable formulations. Such formulations can further comprise one or more additional ingredients including suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions can be prepared, packaged, or sold in the form of a sterile injectable aqueous or oily suspension or solution. This suspension or solution can be formulated according to the known art, and can comprise, in addition to the active ingredient, additional ingredients such as the dispersing agents, wetting agents, or suspending agents described herein. Such sterile injectable formulations can be prepared using a non-toxic parenterally-acceptable diluent or solvent, such as water or 1,3-butanediol, for example. Other acceptable diluents and solvents include Ringer's solution, isotonic sodium chloride solution, and fixed oils such as synthetic mono- or diglycerides. Other parentally-administrable formulations which are useful include those which comprise the active ingredient in microcrystalline form, in a liposomal preparation, or as a component of a biodegradable polymer systems. Compositions for sustained release or implantation can comprise pharmaceutically acceptable polymeric or hydrophobic materials such as an emulsion, an ion exchange resin, a sparingly soluble polymer, or a sparingly soluble salt.

These compositions may also contain adjuvants such as preserving, wetting, emulsifying, and/or dispersing agents. Preventing microorganism contamination of the compositions can be accomplished by the addition of various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and/or gelatin.

Dosage forms can include solid or injectable implants or depots. In preferred embodiments, the implant comprises an effective amount of an active agent and a biodegradable polymer. In preferred embodiments, a suitable biodegradable polymer can be selected from the group consisting of a polyaspartate, polyglutamate, poly(L-lactide), a poly(D,L-lactide), a poly(lactide-co-glycolide), a poly(ε-caprolactone), a polyanhydride, a poly(beta-hydroxy butyrate), a poly(ortho ester) and a polyphosphazene. In other embodiments, the implant comprises an effective amount of active agent and a silastic polymer. The implant provides the release of an effective amount of active agent for an extended period of about one week to several years.

Solid dosage forms for oral administration include capsules, tablets, powders, and granules. In such solid dosage forms, the active compound is admixed with at least one inert customary excipient (or carrier) such as sodium citrate or dicalcium phosphate or (a) fillers or extenders, as for example, starches, lactose, sucrose, mannitol, or silicic acid; (b) binders, as for example, carboxymethylcellulose, alginates, gelatin, polyvinylpyrrolidone, sucrose, or acacia; (c) humectants, as for example, glycerol; (d) disintegrating agents, as for example, agar-agar, calcium carbonate, potato or tapioca starch, alginic acid, certain complex silicates, or sodium carbonate; (e) solution retarders, as for example, paraffin; (f) absorption accelerators, as for example, quaternary ammonium compounds; (g) wetting agents, as for example, cetyl alcohol or glycerol monostearate; (h) adsorbents, as for example, kaolin or bentonite; and/or (i) lubricants, as for example, talc, calcium stearate, magnesium stearate, solid polyethylene glycols, sodium lauryl sulfate, or mixtures thereof. In the case of capsules and tablets, the dosage forms may also comprise buffering agents.

A tablet comprising the active ingredient can, for example, be made by compressing or molding the active ingredient, optionally with one or more additional ingredients. Compressed tablets can be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets can be made by molding, in a suitable device, a mixture of the active ingredient, a pharmaceutically acceptable carrier, and at least sufficient liquid to moisten the mixture.

Pharmaceutically acceptable excipients used in the manufacture of tablets include inert diluents, granulating and disintegrating agents, binding agents, and lubricating agents. Known dispersing agents include potato starch and sodium starch glycolate. Known surface active agents include sodium lauryl sulfate. Known diluents include calcium carbonate, sodium carbonate, lactose, microcrystalline cellulose, calcium phosphate, calcium hydrogen phosphate, and sodium phosphate. Known granulating and disintegrating agents include corn starch and alginic acid. Known binding agents include gelatin, acacia, pre-gelatinized maize starch, polyvinylpyrrolidone, and hydroxypropyl methylcellulose. Known lubricating agents include magnesium stearate, stearic acid, silica, and talc.

Tablets can be non-coated or they can be coated using known methods to achieve delayed disintegration in the gastrointestinal tract of a human, thereby providing sustained release and absorption of the active ingredient. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Tablets can further comprise a sweetening agent, a flavoring agent, a coloring agent, a preservative, or some combination of these in order to provide pharmaceutically elegant and palatable preparation.

Solid dosage forms such as tablets, dragees, capsules, and granules can be prepared with coatings or shells, such as enteric coatings and others well known in the art. They may also contain opacifying agents, and can also be of such composition that they release the active compound or compounds in a delayed manner. Examples of embedding compositions that can be used are polymeric substances and waxes. The active compounds can also be in micro-encapsulated form, if appropriate, with one or more of the above-mentioned excipients.

Solid compositions of a similar type may also be used as fillers in soft or hard filled gelatin capsules using such excipients as lactose or milk sugar, as well as high molecular weight polyethylene glycols, and the like. Hard capsules comprising the active ingredient can be made using a physiologically degradable composition, such as gelatin. Such hard capsules comprise the active ingredient, and can further comprise additional ingredients including, for example, an inert solid diluent such as calcium carbonate, calcium phosphate, or kaolin. Soft gelatin capsules comprising the active ingredient can be made using a physiologically degradable composition, such as gelatin. Such soft capsules comprise the active ingredient, which can be mixed with water or an oil medium such as peanut oil, liquid paraffin, or olive oil.

Oral compositions can be made, using known technology, which specifically release orally-administered agents in the small or large intestines of a human patient. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., Aliment. Pharmacol. Therap. (1987) 1:273-280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., J. Med. Chem. (1984) 27:261-268) and a variety of naturally available and modified polysaccharides (see PCT application PCT/GB89/00581) can be used in such formulations.

Pulsed release technology such as that described in U.S. Pat. No. 4,777,049 can also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, isotonic saline, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, almond oil, arachis oil, coconut oil, cottonseed oil, groundnut oil, corn germ oil, olive oil, castor oil, sesame seed oil, MIGLYOL™, glycerol, fractionated vegetable oils, mineral oils such as liquid paraffin, tetrahydrofurfuryl alcohol, polyethylene glycols, fatty acid esters of sorbitan, or mixtures of these substances, and the like.

Besides such inert diluents, the composition can also include adjuvants, such as wetting agents, emulsifying and suspending agents, demulcents, preservatives, buffers, salts, sweetening, flavoring, coloring and perfuming agents. Suspensions, in addition to the active compound, may contain suspending agents, as for example, ethoxylated isostearyl alcohols, polyoxyethylene sorbitol or sorbitan esters, microcrystalline cellulose, hydrogenated edible fats, sodium alginate, polyvinylpyrrolidone, gum tragacanth, gum acacia, agar-agar, and cellulose derivatives such as sodium carboxymethylcellulose, methylcellulose, hydroxypropylmethylcellulose, aluminum metahydroxide, bentonite, or mixtures of these substances, and the like. Liquid formulations of a pharmaceutical composition of the invention that are suitable for oral administration can be prepared, packaged, and sold either in liquid form or in the form of a dry product intended for reconstitution with water or another suitable vehicle prior to use.

Known dispersing or wetting agents include naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include lecithin and acacia. Known preservatives include methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents can be prepared in substantially the same manner as liquid suspensions, the primary difference being that the active ingredient is dissolved, rather than suspended in the solvent. Liquid solutions of the pharmaceutical composition of the invention can comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Compositions for rectal or vaginal administration can be prepared by mixing an antifungal compound and any additional compounds with suitable non-irritating excipients or carriers such as cocoa butter, polyethylene glycol or a suppository wax, which are solid at ordinary room temperature, but liquid at body temperature, and therefore, melt in the rectum or vaginal cavity and release the antifungal. Such a composition can be in the form of, for example, a suppository, a retention enema preparation, and a solution for rectal or colonic irrigation. Suppository formulations can further comprise various additional ingredients including antioxidants and preservatives. Retention enema preparations or solutions for rectal or colonic irrigation can be made by combining the active ingredient with a pharmaceutically acceptable liquid carrier. As is known in the art, enema preparations can be administered using, and can be packaged within, a delivery device adapted to the rectal anatomy of a human. Enema preparations can further comprise various additional ingredients including antioxidants and preservatives.

A pharmaceutical composition of the invention can be prepared, packaged, or sold in a formulation suitable for vaginal administration. Such a composition can be in the form of, for example, a suppository, an impregnated or coated vaginally-insertable material such as a tampon, a douche preparation, or a solution for vaginal irrigation.

Dosage forms for topical administration of an antifungal compound include ointments, powders, sprays and inhalants. The compounds are admixed under sterile conditions with a physiologically acceptable carrier, and any preservatives, buffers, and/or propellants that may be required. Formulations suitable for topical administration include liquid or semi-liquid preparations such as liniments, lotions, oil-in-water or water-in-oil emulsions such as creams, ointments or pastes, and solutions or suspensions. Topically-administrable formulations can, for example, comprise from about 0.1% to about 10% (w/w) active ingredient, although the concentration of the active ingredient can be as high as the solubility limit of the active ingredient in the solvent. Formulations for topical administration can further comprise one or more of the additional ingredients described herein.

Ophthalmic formulations, eye ointments, powders, and solutions are also contemplated as being within the scope of this invention. Such formulations can, for example, be in the form of eye drops including, for example, a 0.1-1.0% (w/w) solution or suspension of the active ingredient in an aqueous or oily liquid carrier. Such drops can further comprise buffering agents, salts, or one or more other of the additional ingredients described herein. In other embodiments, ophthalmalmically administrable formulations comprise the active ingredient in microcrystalline form or in a liposomal preparation.

Pharmaceutical compositions of the invention formulated for pulmonary delivery can provide the active ingredient in the form of droplets of a solution or suspension. Such formulations can be prepared, packaged, or sold as aqueous or dilute alcoholic solutions or suspensions, optionally sterile, comprising the active ingredient, and can conveniently be administered using any nebulization or atomization device. Such formulations can further comprise one or more additional ingredients including a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

A pharmaceutical composition of the invention can be prepared, packaged, or sold in a formulation suitable for buccal administration. Such formulations can, for example, be in the form of tablets or lozenges made using conventional methods, and can, for example, comprise 0.1 to 20% (w/w) active ingredient, the balance comprising an orally dissolvable or degradable composition and, optionally, one or more of the additional ingredients described herein. Alternately, formulations suitable for buccal administration can comprise a powder or an aerosolized or atomized solution or suspension comprising the active ingredient. Such powdered, aerosolized, or atomized formulations, when dispersed, preferably have an average particle or droplet size in the range from about 0.1 to about 200 nanometers, and can further comprise one or more of the additional ingredients described herein.

For parenteral administration in non-human animals, the compound or compounds may be prepared in the form of a paste or a pellet and administered as an implant, usually under the skin of the head or ear of the animal. Paste formulations can be prepared by dispersing a compound or compounds in pharmaceutically acceptable oil such as peanut oil, sesame oil, corn oil or the like. Pellets containing a therapeutically effective amount of a compound or compounds can be prepared by admixing the compound with a diluent such as a carbowax, carnauba wax, and the like, and a lubricant, such as magnesium or calcium stearate, can be added to improve the pelleting process. It is, of course, recognized that more than one pellet may be administered to an animal to achieve the desired dose level. Moreover, it has been found that such implants may also be administered periodically during the animal treatment period in order to maintain the proper active agent level in the animal's body.

The antifungal compounds of the present invention and the pharmaceutically acceptable salts of the same, can be administered to a patient at dosage levels in the range of from about 0.01 to about 1,000 mg per day. For a normal adult human having a body weight of about 70 kg, a dosage in the range of from about 0.01 to about 300 mg is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

It is not critical whether the compound is administered directly to the cell, to a tissue comprising the cell, a body fluid that contacts the cell, or a body location from which the compound can diffuse or be transported to the cell. It is sufficient that the compound is administered to the patient in an amount and by a route whereby an amount of the compound sufficient to mobilize lipids in the cell arrives, directly or indirectly at the cell. The minimum amount varies with the identity of the antifungal compound.

In preferred embodiments, a pharmaceutical composition comprising an antifungal compound can be administered to a patient at dosage levels in the range of about 0.1 to about 7,000 mg per day. A preferred dosage range is about 1 to about 100 mg per day. In other embodiments, a pharmaceutical composition comprising an antifungal can be administered to deliver a dose of between one nanogram per day per kilogram body weight and 100 milligrams per day per kilogram body weight, preferably from about 0.1 to about 10 mg/kg body weight of the individual per day, and preferably to deliver of between 100 milligrams and 2 grams, to a human patient.

The specific dosage and dosage range that can be used depends on a number of factors, including the requirements of the patient, the severity of the condition being treated, and the pharmacological activity of the compound being administered. The determination of dosage ranges and optimal dosages for a particular patient is well within the ordinary skill of one in the art in view of this disclosure. It is understood that the ordinarily skilled physician or veterinarian will readily determine and prescribe an effective amount of the compound to mobilize lipid stores, induce weight loss, or inhibit appetite in the patient. In so proceeding, the physician or veterinarian can, for example, prescribe a relatively low dose at first, subsequently increasing the dose until an appropriate response is obtained. It is further understood, however, that the specific dose level for any particular human will depend upon a variety of factors including the activity of the specific compound employed, the age, body weight, general health, gender, and diet of the human, the time of administration, the route of administration, the rate of excretion, any drug combination, and the severity of any disorder being treated.

The following examples are offered for illustrative purposes only and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

β-Peptide Synthesis

Materials. Fmoc-(S,S)-trans-2-aminocyclohexanecarboxylic acid was synthesized as described by Schinnerl et al. (*Eur. J. Org. Chem.* 2003, 721-726). Fmoc-(S)-β$^3$Tyr-OH, Fmoc-(S)-β³Lys(Boc)-OH, Fmoc-(S)-β³Val-OH, Fmoc-(S)-β³Phe-OH, and Fmoc-(S)-β³Leu-OH were prepared as described by Seebach et al. (*Helv. Chim. Acta* 1996, 79, 913-941). NovaSyn TGR resin (0.25 mmol/g loading) and O-benzo-triazol-1-yl-N,N,N',N'-tetramethyluronium hexafluorophosphate (HBTU) were purchased from Novabiochem. Methanol, dichloromethane (DCM), and acetonitrile were purchased from Burdick & Jackson. Biotech grade N,N-dimethylformamide (DMF) was purchased from Aldrich and stored over 50W-X8 DOWEX ion-exchange resin, and dry N,N-diidopropylethylamine (DIEA) was distilled from calcium hydride. The remaining reagents were used as purchased from Aldrich.

β-Peptide preparation. β-Peptides were prepared with Fmoc solid-phase synthesis methods utilizing a microwave reactor (CEM, MARS system) to reduce reaction times and increase yield (see, e.g., Murray, J. K.; Gellman, S. H. *Org. Lett.* 2005, 7, 1517-1520). β-Peptides were synthesized from the C-terminal end to the N-terminal end on NovaSyn TGR resin, typically at a 10 μmol scale. Reactions took place at atmospheric pressure with magnetic stirring. Microwave irradiation used 600 W maximum power, and the temperature was measured with a fiber optic temperature sensor. Resin was placed in a solid phase extraction tube (Alltech), swelled in DCM, and washed three times with DMF prior to coupling the first residue.

For a 10 μmol scale synthesis, the first β-amino acid residue (30 μmol) being coupled was activated using 60 μL of 0.5 M HBTU in DMF, 440 μL of DMF, 60 μL, of 0.5 M 1-hydroxybenzotriazole (HOBt) in DMF, and 60 μL of 1.0 M DIEA in DMF, and the activated residue were added to the swelled resin. The residue was coupled using microwave irradiation to ramp the reaction temperature to 80° C. over two minutes and hold the temperature at 80° C. for four minutes. The resin was washed (3 times with DMF, 3 times with DCM, 3 times with DMF) after coupling, and 750 μL of 20% piperidine in DMF (v/v) deprotection solution was added. The residue was deprotected in the microwave by ramping to 90° C. over two minutes and holding for two minutes. The resin was washed (3 times with DMF, 3 times with DCM, 3 times with DMF) after deprotection, and the coupling and deprotection steps were repeated for the next residue.

When coupling an ACHC residue beyond the first two residues of the β-peptide, the residue was coupled two times and then deprotected two times, due to the difficulty of such reactions. In addition, for ACHC residues beyond the first three residues, an additional step of temperature ramping (three stages of two minute ramps to 80° C. with ten minute holds at 80° C. between the ramping stages) was employed before the double deprotection.

The coupling and deprotection steps were repeated until all of the residues were coupled, and then the resin was washed (3 times with DMF, 3 times with DCM, and 3 times with methanol) after the deprotection step for the final residue. β-Peptides were cleaved from the resin and side chains were deprotected using a 95% trifluoroacetic acid (TFA), 2.5% triisopropylsilane, and 2.5% water solution, and the crude peptide was dried under a nitrogen stream.

Purification and characterization. After synthesis, β-peptides were purified using reversed-phase high pressure liquid chromatography (HPLC) on a Vydac C18 semipreparative column. The flow rate was 3 mL/min, and solvents were 0.1% trifluoroacetic acid (TFA) in water (solvent A) and 0.1% TFA in acetonitrile (solvent B). Solvent gradients for the purification of each peptide are given in Table 2. A Vydac C18 analytical column with a flow rate of 1 mL/min and a linear gradient of 10-60% solvent B over 50 minutes was used to evaluate the purity of the β-peptides.

Matrix-assisted laser desorption/ionization time-of-flight (MALDI-TOF) mass spectroscopy (Bruker Reflex II, 337 nm laser) was used to determine β-peptide mass. The matrix was α-cyano-4-hydroxycinnamic acid, and data were calibrated with angiotensin $(M+H^+)=1296.7$ and neurotensin $(M+H^+)=1672.9$. The calculated β-peptide masses and those determined from MALDI-TOF mass spectroscopy are shown in Table 2. Following purification and molecular weight confirmation, peptides were lyophilized for use in the biological assays and circular dichroism analysis.

TABLE 2

Solvent gradients for HPLC purification of β-peptides and masses of β-peptides calculated from chemical formulas and determined from MALDI-TOF mass spectroscopy.

| β-peptide | Solvent gradient (% B over 20 min) | Calculated mass | | MALDI-TOF mass | | |
|---|---|---|---|---|---|---|
| | | Formula | M | $(M + H^+)$ | $(M + Na^+)$ | $(M + K^+)$ |
| 1 | 42-52% | $C_{70}H_{122}N_{14}O_{11}$ | 1334.9 | 1336.0 | 1358.0 | 1374.0 |
| 2 | 44.5-55.5% | $C_{73}H_{128}N_{14}O_{11}$ | 1377.0 | 1378.2 | 1400.2 | 1416.2 |
| 3 | 44-54% | $C_{82}H_{122}N_{14}O_{11}$ | 1478.9 | 1479.7 | 1501.7 | 1517.7 |
| 4 | 38-48% | $C_{67}H_{122}N_{14}O_{11}$ | 1298.9 | 1299.9 | 1321.9 | 1337.8 |
| 5 | 37-47% | $C_{73}H_{122}N_{14}O_{11}$ | 1370.9 | 1371.9 | 1393.9 | 1409.8 |
| 6 | 37-47% | $C_{60}H_{111}N_{13}O_{9}$ | 1157.9 | 1158.9 | 1180.9 | 1196.9 |
| 7 | 21-31% | $C_{60}H_{111}N_{13}O_{9}$ | 1157.9 | 1158.6 | 1180.7 | 1196.6 |

Circular Dichroism (CD) Analysis

Samples were prepared by weighing lyophilized β-peptides into Eppendorf tubes and dissolving in Millipore water to yield a concentration of approximately 1 mM. β-Peptide solutions were then diluted 10-fold with an aqueous TRIS-buffered solution to give a final concentration of approximately 0.1 mM β-peptide in 10 mM Tris (pH 7.3). The final concentration of each β-peptide solution was determined by the solution's UV absorbance. The extinction coefficient of each β-peptide at 275 nm was estimated to be 1420 cm$^{-1}$ mol$^{-1}$, based on the extinction coefficient of α-tyrosine (Creighton, T. E. *Proteins: Structures and Molecular Principles*, 2$^{nd}$ ed.; W. H. Freeman and Company: New York, 1993; p 14). Circular dichroism spectra were recorded on an Aviv 202SF spectrometer at room temperature using a 1-mm path length cell and 5 second averaging times. The CD signal resulting from the buffer alone was subtracted from the spectrum of each β-peptide solution. Data were converted to ellipticity (deg cm$^2$ dmol$^{-1}$) according to the equation:

$$[\Theta]=\Psi/(1000nlc)$$

where Ψ is the CD signal in degrees, n is the number of amides, l is the path length in centimeters, and c is the concentration in decimoles per cm³.

Biological Assays

Minimum inhibitory concentration assay. Minimum inhibitory concentrations (MIC) for the β-peptides were determined using the broth microdilution assay described by the Committee for Clinical and Laboratory Standards (formerly known as the National Committee for Clinical Laboratory Standards) (National Committee for Clinical Laboratory Standards *Reference method for broth dilution antifungal susceptibility testing of yeasts: approved standard—second edition*; NCCLS document M27-A2; NCCLS: Wayne, Pa., 2002). Three strains of *Candida albicans* were used: SC5314, ATCC 24433, and ATCC 90028. Cells were grown for 24 hours on Sabouraud dextrose agar at 30° C. After 24 hours of growth, the cells were suspended in 0.145 M saline, and the concentration was adjusted to between $1 \times 10^6$ cells/mL and $5 \times 10^6$ cells/mL in saline. The working suspension was obtained by diluting the suspension 1:1000 in RPMI 1640 (with L-glutamine and without sodium bicarbonate, Invitrogen) buffered with 0.145 mol/L 3-(N-morpholino) propanesulfonic acid (MOPS).

Twofold serial dilutions of stock solutions of α- or β-peptides or amphotericin B (Calbiochem, solubilized in dimethyl sulfoxide) were made in RPMI 1640, and 100 μL aliquots were put into 96-well plates (Falcon). An equal volume of the cell suspension was added to the wells for a total volume of 200 μL. Growth controls and sterility controls were included.

Plates were incubated at 35° C. for 48 h and then visually inspected for fungal growth. The MIC was defined as the lowest concentration of peptide or amphotericin B that resulted in no visible growth of *C. albicans*. Experiments were performed in duplicate and repeated on at least two different days.

Hemolysis assay. The hemolysis assay was performed using human red blood cells (hRBC) as described previously (Raguse, et al. *J. Am. Chem. Soc.* 2002, 124, 12774-12785; Porter, et al. *J. Am. Chem. Soc.* 2005, 127, 11516-11529). The hRBC were washed three times in TRIS-buffered saline (TBS; 10 mM TRIS, 150 mM NaCl, pH 7.2) and then diluted to a concentration of 1% (v/v) in TBS. The hRBC suspension (80 μL) was added to twofold dilutions of peptides in TBS (20 μL) in a 96-well plate (Falcon). Wells containing hRBC treated with 20 μL TBS provided a negative control, and wells with high concentrations of the peptide melittin (Sigma) served as a positive control. After incubating at 37° C. for 1 h, plates were centrifuged, and 50 μL of the supernatant was diluted with 50 μL of water in a fresh 96-well plate. The absorbance of the diluted supernatant was measured at 405 nm, and the percent hemolysis for each well was calculated from $$\% \text{ hemolysis} = \frac{A_{405}^{peptide} - A_{405}^{buffer}}{A_{405}^{completelysis} - A_{405}^{buffer}} \cdot 100$$

where $A_{405}^{peptide}$ is the absorbance for the supernatant of hRBC treated with peptide, $A_{405}^{buffer}$ is the absorbance for the supernatant of hRBC in TBS, and $A_{405}^{completelysis}$ is the average absorbance for the supernatant of cells treated with melittin at concentrations of 50-400 μg/mL. Experiments were performed in duplicate on at least two different days.

Biofilm Antifungal Susceptibility Testing

The susceptibility of *Candida albicans* biofilms to β-peptide treatment was evaluated using procedures based on the method described by Ramage and Lopez-Ribot. (Ramage, G.; Lopez-Ribot, J. L. *Methods Mol. Med.* 2005, 118, 71-79). ATCC 90028, ATCC 24433, and SC5314 were grown in liquid yeast peptone dextrose (YPD) medium overnight at 30° C. The cells were washed two times with phosphate-buffered saline (PBS, pH 7.2) and resuspended in RPMI 1640 (with L-glutamine and without sodium bicarbonate, Invitrogen) buffered with 0.145 mol/L 3-(N-morpholino) propanesulfonic acid (MOPS). After adjusting the cell suspension to about $1 \times 10^6$ cells/mL in RPMI 1640, 100 μL of the cell suspension was added to selected wells of flat-bottom 96-well plates (Falcon), leaving the last column of wells empty for background controls. Plates were covered and incubated at 37° C. for 48 hours to allow biofilms to form.

After formation, biofilms were washed three times with 200 μL of PBS per well to remove nonadherent cells. Twofold serial dilutions of β-peptide in RPMI 1640 were made, and 100 μL was added to the biofilms in the first 10 columns of the 96-well plates. RPMI 1640 without antifungal (100 μL) was added to the wells in column 11 to serve as a positive growth control. Plates were covered and incubated at 37° C. for an additional 48 hours and then washed as before.

A solution of 0.5 g/L of 2,3-bis(2-methoxy-4-nitro-5-sulfo-phenyl)-2H-tetrazolium-5-carboxanilide (XTT, Sigma) was prepared, and 10 mM menadione (Sigma) in acetone was added to give a final menadione concentration of 1 μM. The XTT solution (100 μL) was added to each well containing a biofilm and to the empty column of wells. The plates were incubated for 1.5 hours at 37° C. to allow the *C. albicans* cells to reduce the XTT. Following incubation, 75 μL of XTT solution was removed from each well and put into a new 96-well plate to measure the absorbance at 490 nm. The reduction of growth for each concentration of β-peptide was calculated from $$\% \text{ reduction} = 100 \cdot \frac{\left(A_{490}^{no\ drug} - A_{490}^{XTT}\right) - \left(A_{490}^{peptide} - A_{490}^{XTT}\right)}{\left(A_{490}^{no\ drug} - A_{490}^{XTT}\right)},$$

where $A_{490}^{peptide}$ is the average absorbance for wells containing a specified concentration of a β-peptide, $A_{490}^{no\ drug}$ is the average absorbance for wells with biofilms not treated with antifungal, and $A_{490}^{XTT}$ is the average absorbance for wells containing only XTT. At least three replicates were included for each combination of β-peptide and *C. albicans* strains.

Assay for Biofilm Formation in the Presence of β-Peptide

The ability of *Candida albicans* to form biofilms in the presence of β-peptide was tested using a procedure modified from the protocol for testing biofilms pre-formed in 96-well plates. *C. albicans* strain SC5314 was grown in liquid yeast peptone dextrose (YPD) medium overnight at 30° C., and the cells were washed twice with PBS (pH 7.2). Cells were resuspended in RPMI 1640, and the cell concentration was adjusted to about $2 \times 10^6$ cells/mL in RPMI 1640.

Twofold serial dilutions of β-peptide and amphotericin B were prepared in RPMI 1640, and 50 μL of each dilution was added to wells of a 96-well plate. At least three replicates were included. β-Peptide-free control wells were also included. An equal volume of the cell suspension was added to give a final cell concentration of $1 \times 10^6$ cells/mL. Plates were covered and placed in a 37° C. incubator for 48 hours.

After allowing biofilms to form for 48 hours, nonadherent cells were removed from the wells by washing the biofilms three times with 200 μL of PBS per well. A 0.5 g/L XTT solution with 1 μM menadione was prepared, and 100 μL was added to each biofilm formation well and to empty wells for XTT background measurements. The 96-well plate was incubated for 1.5 hours at 37° C., and 75 μL of the solution in the wells was transferred to a new 96-well plate. The absorbance of the solution in each well was measured at 490 nm, and the reduction of growth for biofilms grown in the presence of β-peptide and amphotericin B compared to biofilms grown in medium only was calculated from $$\% \text{ reduction} = 100 \cdot \frac{\left(A_{490}^{no\ drug} - A_{490}^{XTT}\right) - \left(A_{490}^{peptide} - A_{490}^{XTT}\right)}{\left(A_{490}^{no\ drug} - A_{490}^{XTT}\right)},$$

where $A_{490}^{peptide}$ is the average absorbance for wells with biofilms formed in the presence of a specified concentration of β-peptide or amphotericin B, $A_{490}^{no\ drug}$ is the average absorbance for wells with biofilms grown with no β-peptide or amphotericin B, and $A_{490}^{XTT}$ is the average absorbance for wells containing only XTT.

While this invention has been described in conjunction with the various exemplary embodiments outlined above, various alternatives, modifications, variations, improvements, and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. An antifungal composition, comprising:
   (a) an inhibitory amount of a β-peptide having the structure:

$(R^1—R^2—R^3)_3$ wherein $R^1$ is ACHC, and $R^2$ and $R^3$ of each triad are independently selected from β-amino acid residues bearing hydrophobic side chains such that the $R^1—R^2—R^3$ triads in the β-peptide consist of side chains in the sequential pattern ACHC-hydrophobic-hydrophobic, wherein $R^2$ and $R^3$ are independently selected from the group consisting of β³Val, β³Phe, β³Ile, β³Ala, β³Leu, β²Val, β²Phe, β²Ile, β²Ala, β²Leu and β-amino acid residues having an ethyl, n-propyl or n-butyl side chain; and
   (b) a pharmaceutically-acceptable carrier.

2. The antifungal composition according to claim 1 wherein said β-peptide further includes a β³Tyr residue at its N-terminus.

3. The antifungal composition according to claim 1 wherein said β-peptide further includes at least one terminus capping group.

4. An antifungal composition comprising an inhibitory amount of a β-peptide, wherein the β-peptide is selected from the group consisting of (ACHC-β³Val-β³Lys)₃, β³Tyr-(ACHC-β³Val-β³Lys)₃, β³Tyr-(ACHC-β³Leu-β³Lys)₃, β³Tyr-(ACHC-β³Phe-β³Lys)₃, and β³Tyr-(ACHC-β³Val-β³Arg)₃; and
a pharmaceutically-acceptable carrier.

5. A fungal resistant medical article comprising an article selected from a stent, valve, pacemaker, defibrillator, artificial joint, prosthesis, neurostimulator, ventricular assist device, congestive heart failure device, indwelling catheter, insulin pump, incontinence device, cochlear device, or embolic filter, said article at least partially coated with an antifungal composition according to claim 1.

6. A kit comprising a pharmaceutical composition according to claim 1 and a delivery device.

* * * * *